United States Patent
Wong et al.

(10) Patent No.: US 9,238,841 B2
(45) Date of Patent: Jan. 19, 2016

(54) MULTI-BIOMARKER-BASED OUTCOME RISK STRATIFICATION MODEL FOR PEDIATRIC SEPTIC SHOCK

(71) Applicant: CHILDREN'S HOSPITAL MEDICAL CENTER, Cincinnati, OH (US)

(72) Inventors: Hector R. Wong, Cincinnati, OH (US); Christopher John Lindsell, Cincinnati, OH (US); Shelia Salisbury, Lewisburg, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 0 days.

(21) Appl. No.: 14/377,137

(22) PCT Filed: Feb. 7, 2013

(86) PCT No.: PCT/US2013/025223
§ 371 (c)(1),
(2) Date: Aug. 6, 2014

(87) PCT Pub. No.: WO2013/119871
PCT Pub. Date: Aug. 15, 2013

(65) Prior Publication Data
US 2015/0018238 A1 Jan. 15, 2015

Related U.S. Application Data

(60) Provisional application No. 61/595,996, filed on Feb. 7, 2012.

(51) Int. Cl.
G01N 33/53 (2006.01)
G01N 31/00 (2006.01)
C12Q 1/68 (2006.01)
G01N 33/68 (2006.01)

(52) U.S. Cl.
CPC ............ C12Q 1/6888 (2013.01); C12Q 1/6883 (2013.01); G01N 33/68 (2013.01); C12Q 2600/112 (2013.01); C12Q 2600/158 (2013.01); C12Q 2600/16 (2013.01); G01N 2800/26 (2013.01)

(58) Field of Classification Search
CPC .................... A61K 2300/00; C12Q 2563/143; C12Q 2565/633; C12Q 1/6883; G01N 33/6893; G01N 2800/26
See application file for complete search history.

(56) References Cited

U.S. PATENT DOCUMENTS

| 7,645,573 B2 | 1/2010 | Ivey et al. |
| 2003/0194752 A1 | 10/2003 | Anderson et al. |
| 2004/0121343 A1 | 6/2004 | Buechler et al. |
| 2010/0279878 A1 | 11/2010 | Wong |
| 2011/0059858 A1 | 3/2011 | Kas et al. |
| 2011/0312521 A1 | 12/2011 | Chaussabel |
| 2015/0005189 A1 | 1/2015 | Wong et al. |

FOREIGN PATENT DOCUMENTS

| EP | 2085486 A1 | 8/2009 |
| WO | WO-2006/113833 A2 | 10/2006 |
| WO | WO-2008/143890 A2 | 11/2008 |
| WO | WO-2008/143890 A3 | 11/2008 |
| WO | WO-2009/095786 A2 | 8/2009 |
| WO | WO-2009/095786 A3 | 8/2009 |
| WO | WO-2009/095840 A1 | 8/2009 |
| WO | WO-2012/106396 A2 | 8/2012 |
| WO | WO-2012/106396 A9 | 8/2012 |
| WO | WO-2013/119869 A1 | 8/2013 |

OTHER PUBLICATIONS

Kaplan et. al. (Pediatric Critical Care Medicine, Mar. 12, 2011(2), pp. 165-173).*
Standage and Wong (Expert Rev. Anti. Infect. Ther, Jan. 9, 2011(1) pp. 71-79).*
Alder et al., "The pediatric sepsis biomarker risk model: potential implications for sepsis therapy and biology," Expet Rev. Anti Infect. Ther., 2014, pp. 809-816, vol. 12(7).
Allison et al., "Microarray data analysis: from disarray to consolidation and consensus," Nat. Rev. Genet., Jan. 2006, pp. 55-65, vol. 7(1) [abstract only].
Brierley et al., "Clinical practice parameters for hemodynamic support of pediatric and neonatal septic shock: 2007 update from the American College of Critical Care Medicine," Crit. Care Med., 2009, pp. 666-688, vol. 37(2).
Cornell et al., "Mechanisms and regulation of the gene-expression response to sepsis," Pediatrics., Jun. 2010, pp. 1248-1258, vol. 125(6).
Cvijanovich et al., "Validating the genomic signature of pediatric septic shock," Physiol. Genomics., Jun. 12, 2008, pp. 127-134, vol. 34(1).
Czaja et al., "Readmission and late mortality after pediatric severe sepsis," Pediatrics, Mar. 2009, pp. 849-857, vol. 123(3) [abstract only].
Dellinger et al., "Surviving Sepsis Campaign: international guidelines for management of severe sepsis and septic shock: 2008," A26 [abstract only].
Dombrovskiy et al., "Rapid increase in hospitalization and mortality rates for severe sepsis in the United States: a trend analysis from 1993 to 2003," Crit. Care Med., May 2007, pp. 1244-1250, vol. 35(5) [abstract only].
Freishtat et al., "Sepsis Alters the Megakaryocyte-Platelet Transcriptional Axis Resulting in Granzyme B-mediated Lymphotoxicity," Am. J. Respir. Crit. Care Med., 2009, pp. 467-473, vol. 179.
Giuliano et al., "Admission Angiopoietin Levels in Children with Septic Shock," Shock, Dec. 2007, pp. 650-654, vol. 28(6).
Goldstein et al., "International pediatric sepsis consensus conference: definitions for sepsis and organ dysfunction in pediatrics," Pediatr., Crit. Care Med., Jan. 2005, pp. 2-8, vol. 6(1) [abstract only].

(Continued)

*Primary Examiner* — Lisa Cook
(74) *Attorney, Agent, or Firm* — Mintz Levin Cohn Ferris Glovsky and Popeo, P.C.; Muriel Liberto, Esq.

(57) ABSTRACT

The invention provides multi-biomarker based methods to stratify pediatric septic shock patients into high and low risk groups.

8 Claims, 8 Drawing Sheets

(56) References Cited

OTHER PUBLICATIONS

Kaplan et al., "Changes in peroxisome proliferator activated receptor-gamma activity in children with septic shock," Intensive Care Med., Jan. 2010, pp. 123-130, vol. 36(1).
Kaplan et al., "Biomarker discovery and development in pediatric critical care medicine," Pediatr. Crit. Care, Mar. 2011, pp. 165-173, vol. 12(2).
Marshall, "Sepsis: rethinking the approach to clinical research," J. Leukoc. Biol., Mar. 2008, 471-482, vol. 83(3).
Marshall et al., "Biomarkers of sepsis," Crit. Care Med., Jul. 2009, pp. 2290-2298, vol. 37(7) [abstract only].
Maslove et al., "Gene expression profiling in sepsis: timing, tissue, and translational considerations," Trends in Molecular Medicine, Apr. 2014, pp. 204-213, vol. 20(4).
Muller et al., "Logistic regression and CART in the analysis of multimarker studies," Clin. Chim. Acta., Aug. 2008, pp. 1-6, vol. 394(1-2)
Nadel et al., "Drotrecogin alfa (activated) in children with severe sepsis: a multicentre phase III randomised controlled trial," Lancet, Mar. 10, 2007, pp. 836-843, vol. 369(9564) [abstract only].
Nowak et al., Admission Chemokine (C-C motif) Ligand 4 Levels Predict Survival in Pediatric Septic Shock, Pediatr. Crit. Care Med., Mar. 2010, pp. 213-216, vol. 11(2).
Osuchowski et al., "Stratification is the key: inflammatory biomarkers accurately direct immunomodulatory therapy in experimental sepsis," Crit. Care Med., May 2009, pp. 1567-1573, vol. 37(5).
Patent Cooperation Treaty, "International Preliminary Report on Patentability and Written Opinion" in corresponding International application No. PCT/US2013/025223, mailed Aug. 12, 2014, 5 pgs.
Patent Cooperation Treaty, "International Search Report" in corresponding International application No. PCT/US2013/025223, mailed May 30, 2013, 2 pgs.
Pollack et al., "The Pediatric Risk of Mortality III—Acute Physiology Score (PRISM III-APS): a method of assessing physiologic instability for pediatric intensive care unit patients," J Pediatr., Oct. 1997, pp. 575-581, vol. 131(4) [abstract only].
Shanley et al., "Genome-Level Longitudinal Expression of Signaling Pathways and Gene Networks in Pediatric Septic Shock," MOL MED, Sep.-Oct. 2007, pp. 495-508, vol. 13(9-10).
Sharron et al., "Platelets Induce Apoptosis during Sepsis in a Contact-Dependent Manner That Is Inhibited by GPIIb/IIIa Blockade," PLoS ONE, Jul. 2012, p. e41549, vol. 7(7).
Solan et al., "A novel role for matrix metalloproteinase-8 in sepsis," Crit Care Med., Feb. 2012, pp. 379-387, vol. 40(2).
Standage et al., Biomarkers for pediatric sepsis and septic shock, Expert Rev. Anti Infect. Ther., 2011, pp. 71-79.
Sweeney et al., "Recombinant human activated protein C, package labeling, and hemorrhage risks," Crit. Care Med., Jan. 2009, pp. 327-329, vol. 37(1).
Vincent, et al., "Ten reasons why we should NOT use severity scores as entry criteria for clinical trials or in our treatment decisions," Crit Care Med., Jan. 2010, pp. 283-287, vol. 38(1) [abstract only].
Watson et al., "Scope and epidemiology of pediatric sepsis," Pediatr Crit Care Med, 2005, vol. 6(3), (Suppl.).
Watson et al., "The Epidemiology of Severe Sepsis in Children in the United States," Am J Respir Crit Care Med, 2003, pp. 695-701, vol. 167.
Wheeler et al., "Extracellular heat shock protein 60 (Hsp60) levels in children with septic shock," Inflamm Res., May 2007, pp. 216-219, vol. 56(5) [abstract only].
Wheeler et al., "Extracellular hsp70 levels in children with septic shock," Pediatr Crit Care Med. May 2005, pp. 308-311 vol. 6(3) [abstract only].
Wheeler et al., "Serum Neutrophil Gelatinase-associated Lipocalin (NGAL) as a Marker of Acute Kidney Injury in Critically Ill Children with Septic Shock," Crit Care Med., Apr. 2008, pp. 1297-1303, vol. 36(4).

Wong et al., "A Multibiomarker-Based Outcome Risk Stratification Model for Adult Septic Shock," Critical Care Medicine, Apr. 2014, pp. 781-789, vol. 42(4).
Wong et al., "Genome level expression profiles in pediatric septic shock indicate a role for altered zinc homeostasis in poor outcome," Physiol Genomics, Jul. 18, 2007, pp. 146-155, vol. 30(2).
Wong et al., "Genomic expression profiling across the pediatric systemic inflammatory response syndrome, sepsis, and septic shock spectrum," Crit Care Med., May 2009, pp. 1558-1566, vol. 37(5).
Wong et al., "Increased serum nitrite and nitrate concentrations in children with the sepsis syndrome,"Crit Care Med., May 1995, pp. 835-842, vol. 23(5) [abstract only].
Wong et al., "Plasma bactericidal/permeability-increasing protein concentrations in critically ill children with the sepsis syndrome,"Pediatr Infect Dis J., Dec. 1995, pp. 1087-1091, vol. 14(12) [abstract only].
Wong et al., "Testing the Prognostic Accuracy of the Updated Pediatric Sepsis Biomarker Risk Model," PLoS ONE, Jan. 2014, pp. e86242 (6 pgs.), vol. 9(1).
Wong et al., "The pediatric sepsis biomarker risk model," Critical Care, Oct. 1, 2012, p. R174 (9 pgs.), vol. 16.
Wong et al., "The Temporal Version of the Pediatric Sepsis Biomarker Risk Model," PLoS ONE, Mar. 2014, pp. e92121 (7 pgs.), vol. 9(3).
Wong, "Pediatric septic shock treatment: new clues from genomic profiling," Pharmacogenetics, Oct. 2007, pp. 1287-1290, vol. 8(10).
Stephen W Standage et al., "Biomarkers for pediatric sepsis and septic shock", Expert Review of Anti-Infective Therapy, 9(1):71-79 (2011).
Jennifer M.Kaplan et al: "Biomarker discovery and development in pediatric critical care medicine", Pediatric Critical Care Medicine, 12(2):165-173 (2011).
Wong Hector R et al: "Genome-level expression profiles in pediatric septic shock indicate a role for altered zinc homeostasis in poor outcome", Physiological Genomics, American Physiological Society, 30(2):146-155 (2007).
Vermont Clementien L et al:"CC chemokine levels in children with meningococcal sepsis accurately mortality and disease severity", Critical Care, Biomed Central Ltd., 10(1):1-8 (2006).
Hector R Wong et al:"The pediatric sepsis biomarker risk model", Critical Care, Biomed Central Ltd., 16(5):1-9 (2012).
Allen, T.C. et al. (Mar. 2007). "Anti-interleukin 8 autoantibody: interleukin 8 immune complexes visualized by laser confocal microscopy in injured lung," *Arch Pathol Lab Med* 131(3):452-456.
Aneja, R.K. et al. (Oct. 2011). "Differences Between Adult and Pediatric Septic Shock," *Minerva Anestesiologica* 77(10): 986-992.
Che, D. et al. (2011). "Decision tree and ensemble learning algorithms with their applications in bioinformatics," *Adv. Exp. Med. Biol.*, 696:191-199.
Dellinger, R.P. et al. (Feb. 2013). "Surviving sepsis campaign: international guidelines for management of severe sepsis and septic shock: 2012," *Crit. Care Med.* 41(2):580-637.
Kartal, E.D. et al. (Jun. 2012, e-published Jun. 1, 2012). "Several Cytokines and Protein C Levels with the Apache II Scoring System for Evaluation of Patients with Sepsis," *Balkan Medical Journal* 29(2): 174-178.
Hack, E. et al. (Jul. 1992). "Interleukin-8 in relation to shock and inflammatory mediators", *Infection and Immunity, American Society for Microbiology.* 60(7): 2835-2842.
Hanley, J.A. et al. (Sep. 1983). "A method of comparing the areas under receiver operating characteristic curves derived from the same cases," *Radiology* 148(3): 839-843.
Hein, O.V. et al. (2005). "Time course of endothelial damage in septic prediction of outcome," *Critical Care, Biomed Central Ltd.* 9(4): R307-R314.
Livaditi, O. et al. (Dec. 2006, e-published Mar. 26, 2007). "Neutrophil CD64 expression and serum IL-8: sensitive early markers of severity and outcome in sepsis," Cytokine 36(5-6):283-290.
Levy, M.M. et al. (Feb. 2010). "The Surviving Sepsis Campaign: results of an international guideline-based performance improvement program targeting severe sepsis," *Crit. Care Med.* 38(2): 367-374.

(56) References Cited

OTHER PUBLICATIONS

Lokshin, A.E. et al. (Aug. 2006, e-published Jan. 24, 2006). "Circulating IL-8 and anti-IL-8 autoantibody in patients with ovarian cancer," *Gynecol Oncol* 12(2):244-251.

Mera, S. et al. (Feb. 2011, e-published Dec. 10, 2010). "Multiplex cytokine profiling in patients with sepsis," *APMIS* 119(2):155-163.

Nichol, A.D. et al. (2010). "Relative hyperlactatemia and hospital mortality in critically ill patients: a retrospective multi-centre study," *Crit. Care.* 14:R25, 9 pages.

Ranieri, V.M. et al., (May 31, 2012)."Drotrecogin alfa (activated) in adults with septic shock," *N. Engl. J. Med.* 366(22):2055-2064.

Russell, J.A. et al. (Feb. 28, 2008). "Vasopressin versus norepinephrine infusion in patients with septic shock," *N. Engl. J. Med.* 358(9):877-887.

Verboon-Maciolek, M.A. et al. (Mar. 2006). "Inflammatory mediators for the diagnosis and treatment of sepsis in early infancy," *Pediatr Res* 59(3):457-461.

Wacharasint, P. et al. (Jul. 2012). "Normal-range blood lactate concentration in septic shock is prognostic and predictive," *Shock* 38(1):4-10.

Wynn, J. et al. (May 2010). "The host response to sepsis and developmental impact," *Pediatrics* 125(5):1031-1041.

\* cited by examiner

Derivation Cohort Tree

MULTI-BIOMARKER-BASED OUTCOME RISK STRATIFICATION MODEL FOR PEDIATRIC SEPTIC SHOCK

CROSS REFERENCE TO RELATED APPLICATION

The present application is a U.S. National Stage entry under 35 U.S.C. §371 of International Application No. PCT/US2013/025223, filed on Feb. 7, 2013, designating the United States of America and published in English on Aug. 15, 2013, which in turn claims the benefit of priority under 35 U.S.C. §119(e) to U.S. Provisional Application No. 61/595,996, BIOMARKERS OF SEPTIC SHOCK, filed on Feb. 7, 2012, which is currently co-pending herewith and which is incorporated by reference in its entirety.

STATEMENT REGARDING FEDERALLY-SPONSORED RESEARCH

This invention was made with government support under HL100474 and GM064619 awarded by the National Institutes of Health. The government has certain rights in the invention.

FIELD OF THE INVENTION

The invention disclosed herein generally relates to the identification and validatation of clinically relevant, quantifiable biomarkers of diagnostic and therapeutic responses for blood, vascular, cardiac, and respiratory tract dysfunction.

BACKGROUND

Septic shock and severe sepsis represent a major public health problem in the United States, despite the development of increasingly powerful antibiotics and advanced forms of intensive care unit-based support modalities (see, e.g., Shanley, T. et al. *Sepsis*, 3$^{rd}$ Ed., St. Louis, Mo., Mosby (2006)). Worldwide, septic shock affects millions of adults, killing approximately one in four (see, e.g., Dellinger, R. et al. *Crit. Care Med.* 36:296-327 (2008)). A recent study suggests that the incidence and the mortality rates of septic shock in adults are increasing in the United States (Dombrovskiy, V. et al. *Crit. Care Med.* 35:1244-50 (2007)).

Septic shock is also a major problem in the pediatric age group, as there are ~42,000 cases of pediatric septic shock per year in the United States alone, with a mortality rate of ~10% (see, e.g., Watson, R. et al. *Am. J. Respir. Crit. Care Med.* 167:695-701 (2003)). While the pediatric mortality rate is lower than that of adults, it nonetheless translates to more than 4,000 childhood deaths per year and countless years of lost productivity due to death at a young age. While this high number of pediatric deaths per year from septic shock indicates that more children die per year in the United States from septic shock as the primary cause than those children who die from cancer, funding specifically targeted toward pediatric septic shock is substantially lower than that for pediatric cancer.

Reliable stratification of outcome risk is fundamental to effective clinical practice and clinical research (Marshall *J. Leukoc. Biol.* 83:471-82 (2008)). No reliable and widely accepted outcome risk stratification tool specific for septic shock in pediatric patients has heretofore been developed. Such a tool would be beneficial at several levels, including stratification for interventional clinical trials, better-informed decision making for individual patients, and as a metric for quality improvement efforts.

SUMMARY

Embodiments of the invention encompass methods of classifying a pediatric patient with septic shock as high risk or low risk, including: identifying a pediatric patient with septic shock; obtaining a sample from the patient; analyzing the sample to determine the level(s) of one or more biomarkers associated with septic shock in pediatric patients; determining whether the level(s) of the one or more biomarkers are elevated above a cut-off level, wherein the presence of an elevated level of one or more biomarkers associated with septic shock in pediatric patients indicates that the patient has an elevated likelihood of being classified as high risk and the absence of an elevated level of one or more biomarkers associated with septic shock in pediatric patients indicates that the patient has a reduced likelihood of being classified as high risk.

In some embodiments of the methods, the determination of whether the level(s) of the one or more biomarkers are elevated can be combined with one or more patient demographic data and/or clinical characteristics and/or results from other tests or indicia of septic shock. In some embodiments, the patient demographic data includes the age of the patient. In some embodiments, the patient demographic data and/or clinical characteristics and/or results from other tests or indicia of septic shock includes the septic shock causative organism, the presence or absence or chronic disease, and/or the gender, race, and/or co-morbidities of the patient.

In some embodiments, the one or more biomarkers can include CCL3, HSPA1B, IL8, LCN2, ELA2, GZMB, and MMP8. In some embodiments, the one or more biomarkers can include CCL3, LCN2, HSPA1B, IL8, ELA2, MMP8, RETN, THBS, GZMB, ORM1, CCL4, LTF, IL1A, SULF2, and FGL2. In some embodiments, the one or more biomarkers can include the biomarkers listed in Table 1.

In some embodiments, the one or more biomarkers include all of CCL3, HSPA1B, IL8, LCN2, and ELA2. In some embodiments, a classification of high risk includes: a) an elevated level of CCL3, or b) a non-elevated level of CCL3 and an elevated level of HSPA1B, or c) non-elevated levels of CCL3, HSPA1B, and ELA2, and elevated levels of IL8 and LCN2, and a classification of low risk includes: d) non-elevated levels of CCL3, HSPA1B, and IL8, or e) non-elevated levels of CCL3 and HSPA1B, and elevated levels of IL8 and ELA1, or f) non-elevated levels of CCL3, HSPA1B, ELA2, and LCN2, and an elevated level of IL8. In some embodiments, a) an elevated level of CCL3 corresponds to a serum CCL3 concentration greater than 358 pg/ml, b) an elevated level of HSPA1B corresponds to a serum HSPA1B concentration greater than 3.313450 µg/ml, c) an elevated level of IL8 corresponds to a serum IL8 concentration greater than 356 pg/ml, d) an elevated level of ELA2 corresponds to a serum ELA2 concentration greater than 344.596 ng/ml, and e) an elevated level of LCN2 corresponds to a serum LCN2 concentration greater than 8.712 ng/ml.

In some embodiments, the one or more biomarkers include all of CCL3, HSPA1B, IL8, GZMB, and MMP8. In some embodiments, a classification of high risk includes: a) elevated levels of CCL3, IL8, and GZMB, or b) a non-elevated level of IL8 and elevated levels of CCL3 and MMP8, or c) a non-elevated level of GZMB, elevated levels of CCL3 and IL8, and a patient age of 0.5 years or younger, or d) a non-elevated level of CCL3 and an elevated level of HSPA1B, or e) non-elevated levels of CCL3 and HSPA1B, and a highly elevated level of IL8, and a classification of low risk includes: f) non-elevated levels of CCL3 and HSPA1B, and a non-highly elevated level of IL8, or g) non-elevated levels of IL8 and MMP8 and an elevated level of CCL3, or h) a non-elevated level of GZMB, elevated levels of CCL3 and IL8, and a patient age of older than 0.5 years. In some embodiments, a) an elevated level of CCL3 corresponds to a serum CCL3 concentration greater than 160 pg/ml, b) an elevated level of HSPA1B corresponds to a serum HSPA1B concentration greater than 3.27 µg/ml, c) an elevated level of IL8 corresponds to a serum IL8 concentration greater than 507 pg/ml, d) a highly elevated level of IL8 corresponds to a serum IL8 concentration greater than 829 pg/ml, e) an elevated level of GZMB corresponds to a serum GZMB concentration greater than 55 pg/ml, and f) an elevated level of MMP8 corresponds to a serum LCN2 concentration greater than 47.513 ng/ml.

In some embodiments, the determination of whether the level(s) of the one or more biomarkers are elevated above a cut-off level includes applying the patient to a decision tree including the one or more biomarkers. In some embodiments, the patient can be applied to the decision tree depicted in FIG. 2, with terminal nodes 2, 4, and 10 corresponding to a classification of high risk and terminal nodes 5, 8, and 9 corresponding to a classification of low risk. In some embodiments, the patient can be applied to the decision tree depicted in FIG. 8, with terminal nodes 4, 8, 10, 12, and 13 corresponding to a classification of high risk and terminal nodes 7, 11, and 14 corresponding to a classification of low risk.

In some embodiments, the determination of whether the level(s) of the one or more biomarkers are elevated above a cut-off level can be combined with one or more additional population-based risk scores. In some embodiments, the one or more population-based risk scores includes APACHE, PRISM, PIM, and/or PELOD.

In some embodiments, the sample can be obtained within the first hour of presentation with septic shock. In some embodiments, the sample can be obtained within the first 8 hours of presentation with septic shock. In some embodiments, the sample can be obtained within the first 24 hours of presentation with septic shock. In some embodiments, the sample can be obtained within the first 48 hours of presentation with septic shock.

Embodiments of the invention also encompass methods of providing individualized treatment for a pediatric patient with septic shock, wherein a patient classified as high risk via the methods described herein can be selected for one or more high risk therapies, and wherein a patient classified as low risk via the methods described herein can be excluded from one or more high risk therapies. In some embodiments, the one or more high risk therapies include extracorporeal membrane oxygenation/life support, plasmapheresis, pulmonary artery catheterization, and/or high volume continuous hemofiltration. In some embodiments, an outcome can be improved in a pediatric patient with septic shock by providing individualized treatment for a pediatric patient with septic shock, wherein a patient classified as high risk via the methods described herein can be selected for one or more high risk therapies, and wherein a patient classified as low risk via the methods described herein can be excluded from one or more high risk therapies.

Embodiments of the invention also encompass methods of selecting a pediatric patient with septic shock for a clinical trial, wherein a patient classified as high risk via the methods described herein can be selected for a moderate or high risk clinical trial, and wherein a patient classified as low risk via the methods described herein can be excluded from a moderate or high risk clinical trial.

Embodiments of the invention also encompass methods of predicting illness severity in a pediatric patient with septic shock, including: identifying a pediatric patient with septic shock; obtaining a sample from the patient; analyzing the sample to determine the level(s) of one or more biomarkers associated with septic shock in pediatric patients; determining whether the level(s) of the one or more biomarkers are elevated, wherein the presence of an elevated level of one or more biomarkers associated with septic shock in pediatric patients indicates that the patient has a severe case of septic shock and the absence of an elevated level of one or more biomarkers associated with septic shock in pediatric patients indicates that the patient has relatively less severe case of septic shock.

Embodiments of the invention also encompass diagnostic kits, tests, or arrays, including materials for quantification of at least two analytes, wherein the at least two analytes are biomarkers associated with septic shock in pediatric patients, an mRNA corresponding to any member of the group or its receptor, or any combinations thereof. In some embodiments, the at least two analytes can include CCL3, HSPA1B, IL8, LCN2, ELA2, GZMB, and MMP8. In some embodiments, the at least two analytes include all of CCL3, HSPA1B, IL8, LCN2, and ELA2. In some embodiments, the at least two analytes include all of CCL3, HSPA1B, IL8, GZMB, and MMP8. In some embodiments, the at least two analytes can include CCL3, LCN2, HSPA1B, IL8, ELA2, MMP8, RETN, THBS, GZMB, ORM1, CCL4, LTF, IL1A, SULF2, and FGL2. In some embodiments, the at least two analytes can include the biomarkers listed in Table 1.

In some embodiments, the diagnostic kit, test, or array includes a gene chip. In some embodiments, the gene chip includes a low density array. In some embodiments, the diagnostic kit, test, or array includes a surface with a DNA array.

BRIEF DESCRIPTION OF THE DRAWINGS

Those of skill in the art will understand that the drawings, described below, are for illustrative purposes only. The drawings are not intended to limit the scope of the present teachings in any way

Figure 1:
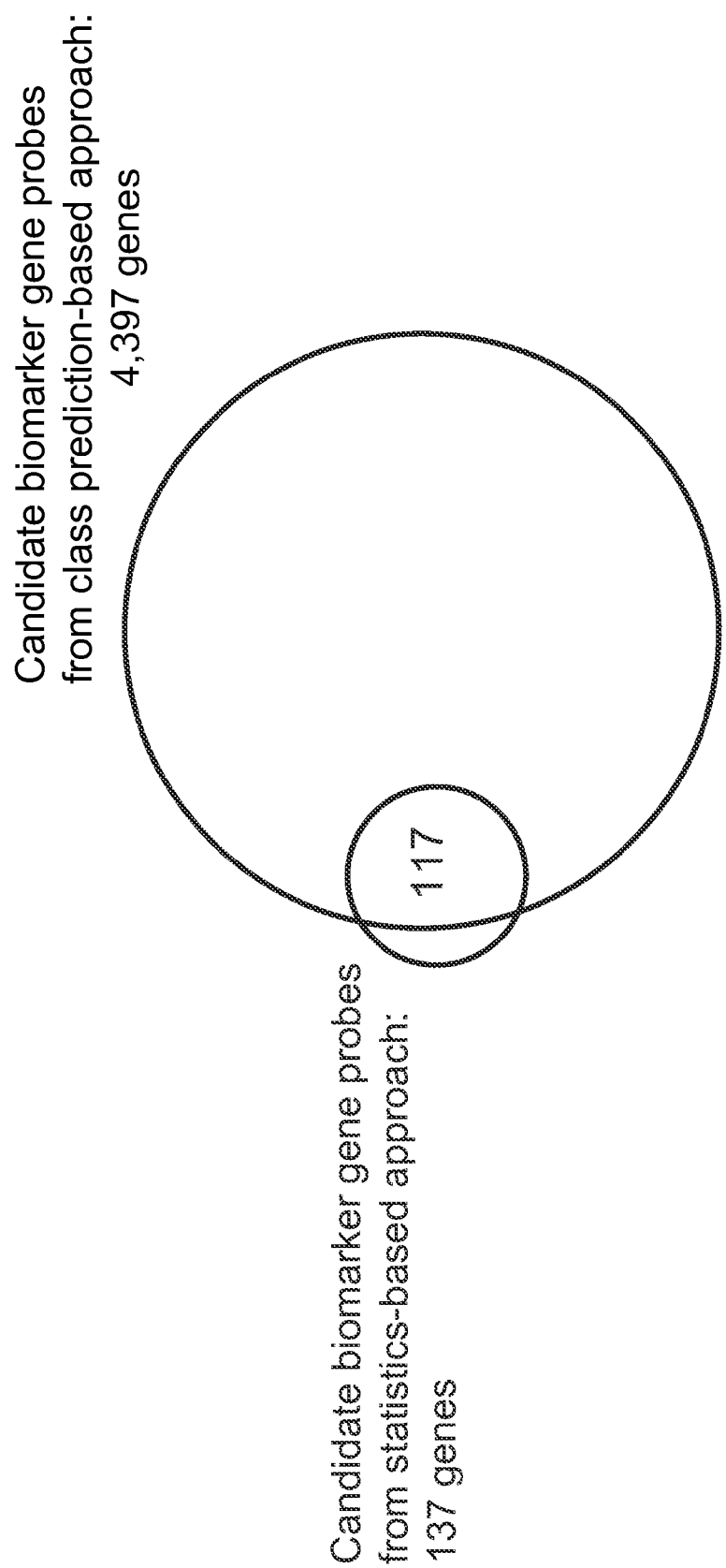
FIG. 1 depicts a Venn analysis showing the 117-gene probe overlap (Table 3) between the 137 candidate biomarker gene probes from the statistics-based approach (Table 1) and the 4,397 candidate biomarker gene probes from the class prediction-based approach (Table 2).

The classification tree consists of five biomarker-based decision rules and ten daughter nodes. The classification tree includes five of the twelve candidate stratification biomarkers: C—C chemokine ligand 3 (CCL3), heat shock protein 70 kDa 1B (HSPA1B), interleukin-8 (IL8), elastase 2 (ELA2), and lipocalin 2 (LCN2). Each node provides the total number of subjects in the node, the biomarker serum concentration-based decision rule, and the number of survivors and non-survivors with the respective rates. For consistency, the serum concentrations of all stratification biomarkers are provided in pg/ml. Terminal nodes 5, 8, and 9 are considered low-risk nodes, whereas terminal nodes 2, 4, 10 are considered high-risk terminal nodes. To calculate the diagnostic test characteristics, all subjects in the low-risk terminal nodes (n=171) were classified as predicted survivors, whereas all subjects in the high-risk terminal nodes (n=49) were classified as predicted non-survivors. The area under the curve (AUC) for the derivation cohort tree was 0.885.

Figure 3:
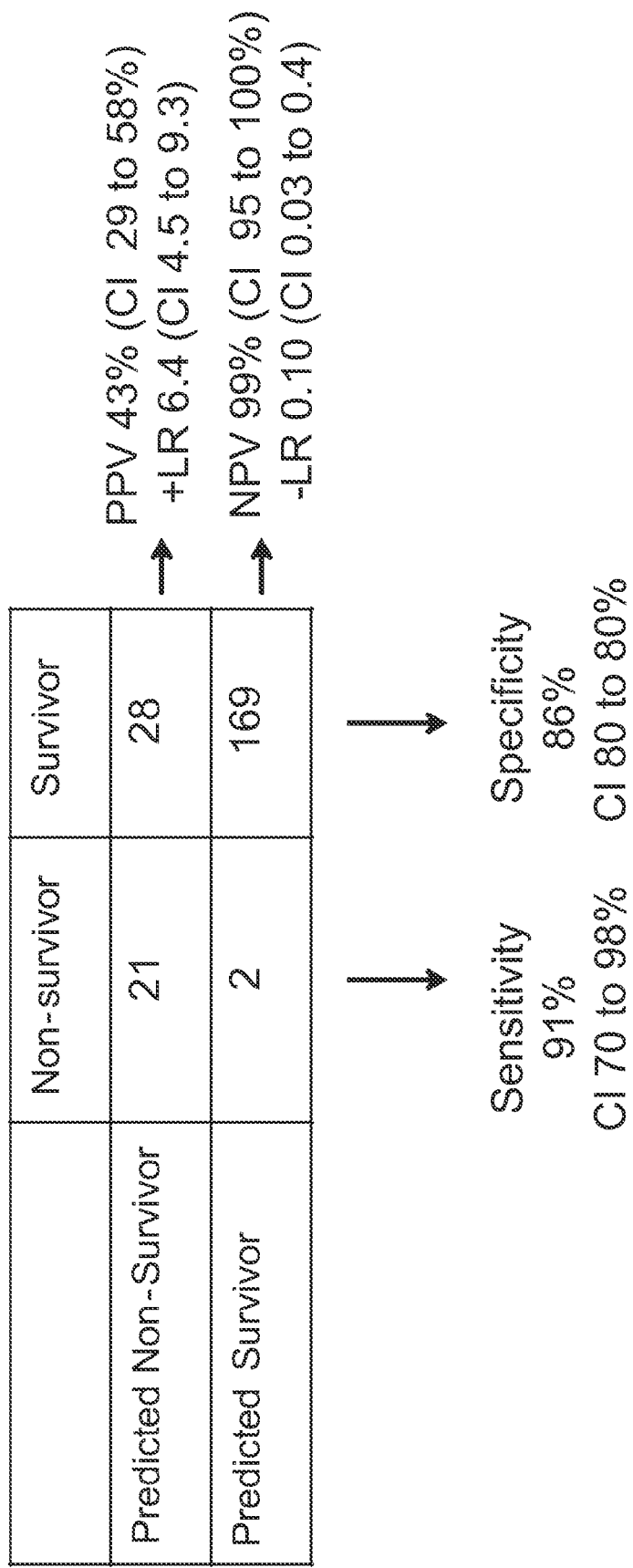

FIG. 3 depicts the 2×2 contingency table for the application of the decision tree to the derivation cohort, showing true positives, true negatives, false positives, and false negatives. This table allows for the calculation of performance characteristics, such as sensitivity, specificity, positive predictive value (PPV), negative predictive value (NPV), likelihood ratio (LR), and confidence interval (CI), as shown. All patients in low risk terminal nodes were predicted as survivors in the contingency table, whereas all patients in high risk nodes were predicted as non-survivors in the contingency table.

Figure 4:
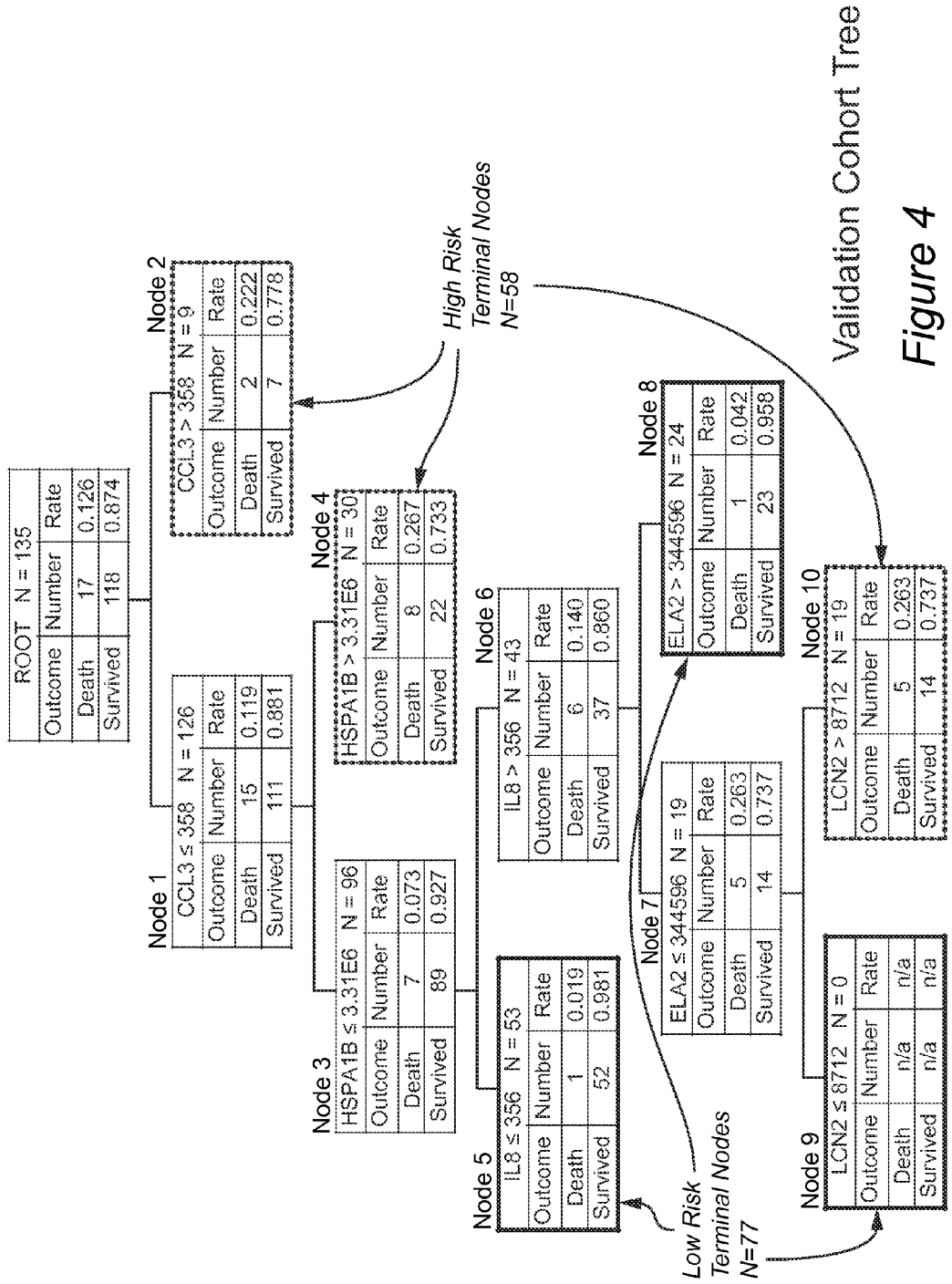

FIG. 4 depicts the test cohort decision tree based on analysis of 5 candidate biomarker gene probes. The decision tree is identical to that generated in the derivation cohort and contains 5 decision rules and 10 daughter nodes, 3 of which are low risk terminal nodes and 3 of which are high risk terminal nodes. The 135 test cohort pediatric patients were "dropped" through the tree using identical decision rules; therefore, the derived classification tree was able to reliably predict outcome in the test cohort.

Figure 5:
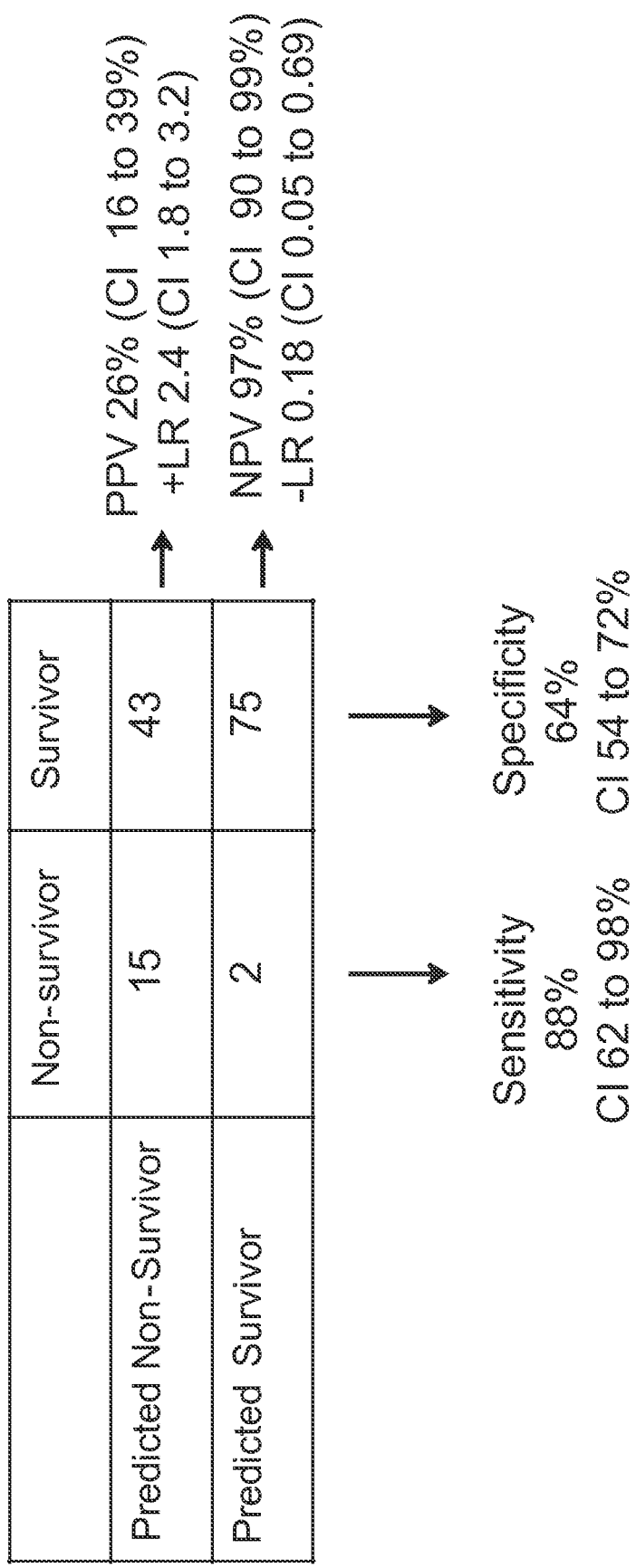

FIG. 5 depicts the 2×2 contingency table for the application of the decision tree to the test cohort, showing true positives, true negatives, false positives, and false negatives. This table allows for the calculation of performance characteristics, such as sensitivity, specificity, PPV, NPV, LR, and CI, as shown. All patients in low risk terminal nodes were predicted as survivors in the contingency table, whereas all patients in high risk nodes were predicted as non-survivors in the contingency table.

Figure 6:
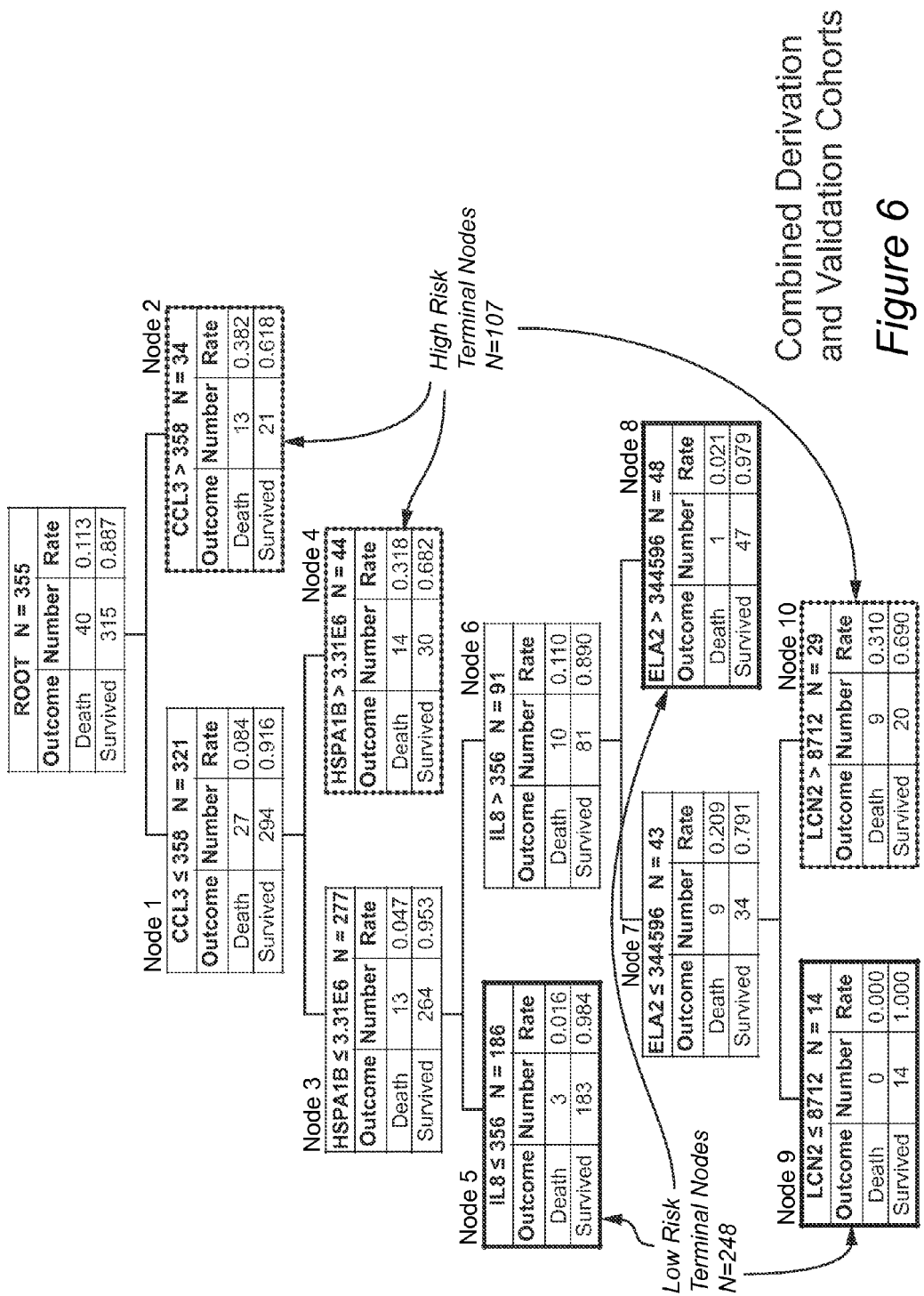

FIG. 6 depicts the combined derivation and test cohort decision tree based on analysis of 5 candidate biomarker gene probes. The decision tree contains 5 decision rules and 10 daughter nodes, 3 of which are low risk terminal nodes and 3 of which are high risk terminal nodes.

Figure 7:
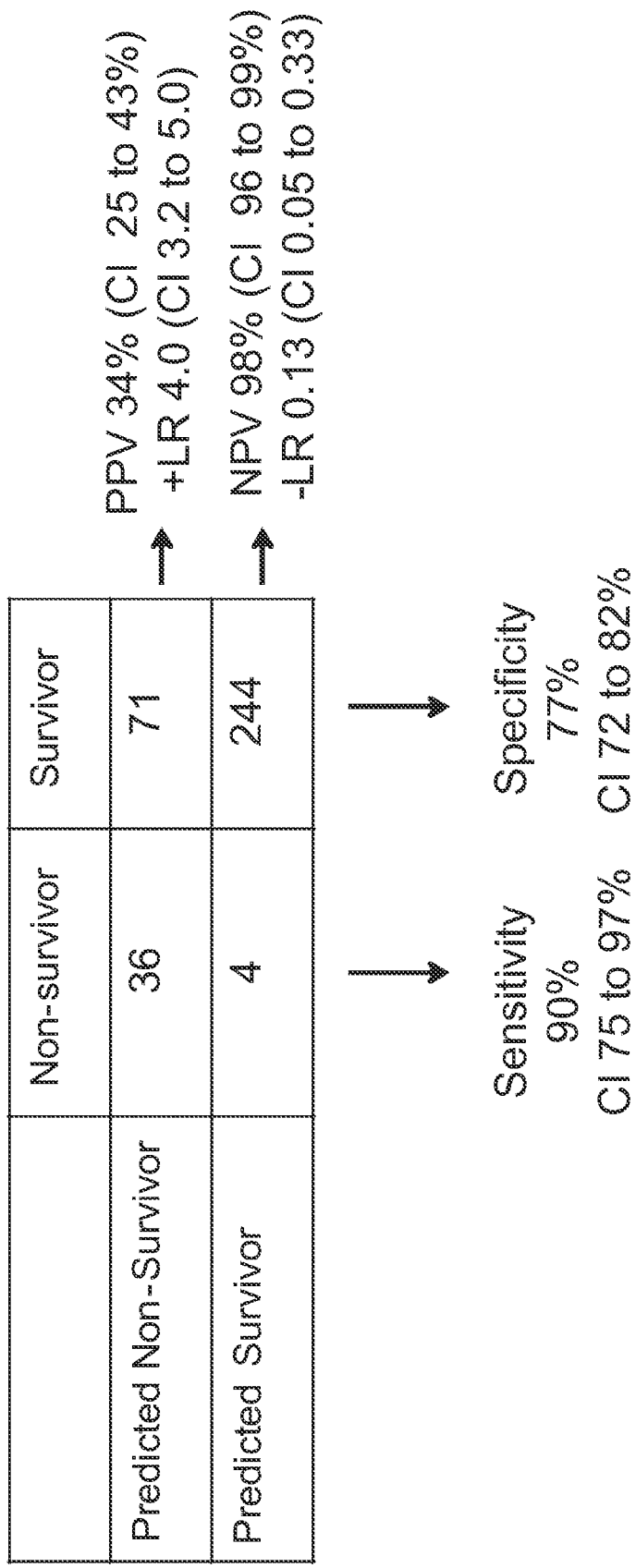

FIG. 7 depicts the 2×2 contingency table for the application of the decision tree to the combined derivation and test cohorts, showing true positives, true negatives, false positives, and false negatives. This table allows for the calculation of performance characteristics, such as sensitivity, specificity, PPV, NPV, LR, and CI, as shown. All patients in low risk terminal nodes were predicted as survivors in the contingency table, whereas all patients in high risk nodes were predicted as non-survivors in the contingency table.

Figure 8:
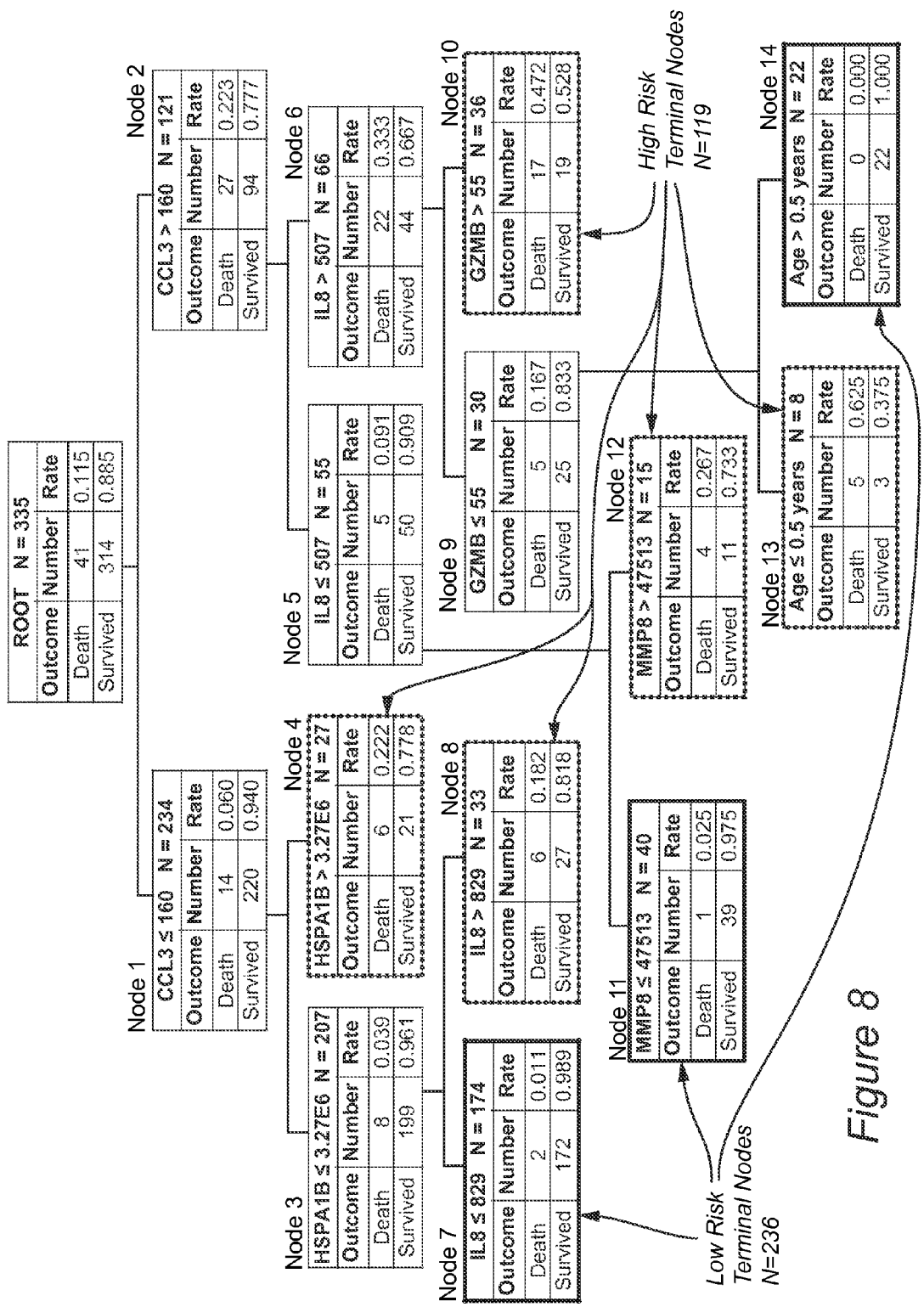

FIG. 8 depicts the classification tree from the updated model based on the combined derivation and test cohorts (n=355). The classification tree consists of six biomarker-based decision rules, one age-based decision rule, and fourteen daughter nodes. The classification tree includes five of the twelve candidate stratification biomarkers: CCL3, HSPA1B, IL8, granzyme B (GZMB), and matrix metalloproteinase-8 (MMP8). Each node provides the total number of subjects in the node, the biomarker serum concentration- or age-based decision rule, and the number of survivors and non-survivors with the respective rates. For consistency, the serum concentrations of all stratification biomarkers are provided in pg/ml. Terminal nodes 7, 11, and 14 are considered low-risk nodes, whereas terminal nodes 4, 8, 10, 12, and 13 are considered high-risk terminal nodes. To calculate the diagnostic test characteristics, all subjects in the low risk terminal nodes (n=236) were classified as predicted survivors, whereas all subjects in the high risk terminal nodes (n=119) were classified as predicted non-survivors. The AUC for the calibrated decision tree was 0.883.

DETAILED DESCRIPTION OF THE INVENTION

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing or monitoring" with reference to septic shock refers to a method or process of determining if a subject has or does not have septic shock or determining the severity or degree of septic shock.

As used herein, "outcome" can refer to the primary outcome studied, typically 28-day survival/mortality. The importance of survival/mortality in the context of pediatric septic shock is readily evident. The common choice of 28 days was based on the fact that 28-day mortality is a standard primary endpoint for interventional clinical trials involving critically ill patients.

As used herein, "outcome" can also refer to the secondary outcome studied, namely resolution of organ failure after 14 days or 28 days or limb loss. Although mortality/survival is obviously an important outcome, survivors have clinically relevant short- and long-term morbidities that impact quality of life, which are not captured by the dichotomy of "alive" or "dead." In the absence of a formal, validated quality of life measurement tool for survivors of pediatric septic shock, resolution of organ failure was tracked as a secondary outcome measure. Specifically, the presence or absence of new organ failure over two timeframes was tracked: 14 days after admission and 28 days after admission. Patients having organ failure beyond 28 days are likely to survive with significant morbidities having negative consequences for quality of life.

Organ failure was defined based on published and well-accepted criteria for the pediatric population (Goldstein, B. et al. *Pediatr. Crit. Care Med.* 6:208 (2005)). Specifically, cardiovascular, respiratory, renal, hepatic, hematologic, and neurologic failure were tracked. In addition, limb loss was tracked as a secondary outcome. Although limb loss is not a true "organ failure," it is an important consequence of pediatric septic shock with obvious impact on quality of life.

As used herein, the terms "predicting outcome" and "outcome risk stratification" with reference to septic shock refers to a method or process of prognosing a patient's risk of a certain outcome. In some embodiments, predicting an outcome relates to determining a relative risk of mortality. Such mortality risk can be high risk, moderate risk, moderate-high risk, moderate-low risk, or low risk. Alternatively, such mortality risk can be described simply as high risk or low risk, corresponding to high risk of death or high likelihood of survival, respectively. As related to the terminal nodes of the decision trees described herein, a "high risk terminal node" corresponds to a high mortality probability, whereas a "low risk terminal node" corresponds to a low mortality probability.

As used herein, the term "high risk clinical trial" refers to one in which the test agent has "more than minimal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient. In some embodiments, a subject is a pediatric patient. In some embodiments, a pediatric patient is a patient under 18 years of age, while an adult patient is 18 or older.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "decision tree" refers to a standard machine learning technique for multivariate data analysis and classification. Decision trees can be used to derive easily interpretable and intuitive rules for decision support systems.

In developed countries with ready access to powerful antibiotics and modern intensive care units, septic shock continues to be a major cause of morbidity and mortality in both adult and pediatric populations (Czaja, A., et al. *Pediatrics*, 123:849-57 (2009); Dellinger, R., et al. *Crit. Care Med.*, 36:296-327 (2008); Dombrovskiy, V., et al. *Crit. Care Med.*, 35:1244-50 (2007); Watson, R., et al. *Am. J. Resp. Grit. Care Med.*, 167:695-701 (2003)). Septic shock is a highly heterogeneous syndrome having variable expression in a given patient cohort. Dating from the 1990s, many clinical trials have been conducted to evaluate potential novel therapies for septic shock, and experimental therapies continue to be evaluated. However, with the exception of one therapy which now has FDA-approved specific labeling for septic shock in adults, namely activated protein C, the majority of experimental therapies fail to demonstrate efficacy when tested in randomized, controlled trials, despite being based on sound biological principles and quality preclinical data (see, e.g., Sweeney, D. et al. *Intensive Care Med.* 37:666-88 (2009); Marshall, J. *J. Leukoc. Biol.*, 82:471-82 (2008)). The above-mentioned activated protein C therapy, namely Xigris (Eli Lilly, Indianapolis, Ind.), has been taken off the market by the manufacturer because a large trial in Europe failed to demonstrate efficacy.

While failure is likely multi-factorial, one consistent confounder is that septic shock is not a simple disease with uniform expression across a given patient cohort. Rather, septic shock is a complex syndrome displaying a tremendous degree of heterogeneity. The intrinsic heterogeneity of clinical septic shock is a major challenge. For clinical trials, individual patient management, and quality improvement efforts, it is unclear which patients are least likely to survive and thus benefit from alternative treatment approaches. Because the inability to manage this heterogeneity presents a major challenge for effective and rational clinical trials, a robust risk stratification tool could overcome this challenge (Marshall, J.

J. Leukoc. Biol., 82:471-82 (2008); Marshall, J. et al. Crit. Care Med., 37:2290-8 (2009)).

In the pediatric age group, a recent randomized trial of activated protein C was terminated early due to futility (Nadel, S. et al. Lancet 369:836-43 (2007)). Thus, septic shock therapy for the pediatric age group is limited solely to prevention (such as vaccines), antibiotics, and intensive care unit-based organ support (see, e.g., Shanley, T. et al. Sepsis, 3$^{rd}$ Ed., St. Louis, Mo., Mosby (2006); Brierley, J., et al. Crit. Care Med. 37:666-88 (2009)).

The reason for failure in clinical trials is presumably not because the biological/physiological principle being tested was fundamentally flawed. Rather, the primary reason for failure lies in the inability to effectively address the substantial heterogeneity that characterizes the syndrome of septic shock. Septic shock is a heterogeneous syndrome with the potential to negatively and directly affect all organ systems relevant to this challenge topic, including blood (coagulopathy), vascular (distributive shock), cardiac (cardiogenic shock), and respiratory (acute respiratory distress syndrome) function. The heterogeneity of septic shock has consistently challenged multiple investigators attempting to evaluate the efficacy of various experimental interventions.

A key challenge in the field is therefore to reduce and manage this heterogeneity by more effectively stratifying patients for the purposes of more rational and effective clinical research and clinical management. Heretofore, no effective way of stratifying pediatric patients who present with septic shock has been developed; an effective stratification process with some qualitative metric could inform decision-making and improve patient outcomes and prospective clinical trial design and management.

The concept of pre-intervention stratification in sepsis, and its positive impact on the efficacy of an experimental therapy, has been corroborated in a murine model of polymicrobial sepsis (Osuchowski, M. et al. Crit. Care Med. 37:1567-73 (2009)). While this study provides proof-of-concept, translating the concept to the bedside of critically ill patients remains a major challenge.

The ability to predict outcome, for individual patients and early in the course of illness, would be a major advancement in clinicians' ability to conduct septic shock interventional clinical trials in a more effective manner. Currently, there is no validated clinical tool that can achieve this important goal. While models that generate mortality prediction scores based on physiological variables, such as the Acute Physiology and Chronic Health Evaluation (APACHE) and Pediatric Risk of Mortality (PRISM) models, can be very effective for estimating population-based outcome risks, these tools are not intended for stratification of individual patients.

A blood protein-derived profile of multiple candidate biomarkers is a clinically feasible and effective strategy for meeting this challenge. Based on a set of biomarkers, selected in an objective and relatively unbiased manner, a multi-biomarker-based risk model can be generated to predict individual patient outcome and illness severity.

As described herein, a multi-biomarker-based risk model (henceforth referred to as PERSEVERE: PEdiatRic SEpsis biomarkEr Risk modEl) to predict outcome in septic shock in pediatric patients has been derived and validated; this model is capable of robustly predicting outcomes, with high sensitivity. When PERSEVERE was applied to an independent cohort of children with septic shock, those predicted as non-survivors had more than 25% mortality by 28 days. Conversely, those predicted as survivors had more than 97% survival by 28 days. Additionally, the high-risk survivors in the updated model were found to have a greater degree of illness severity as measured by persistence of organ failure, pediatric intensive care unit (PICU) length of stay (LOS), and PICU-free days.

The PERSEVERE biomarker panel is an effective, early stratification system for pediatric patients with septic shock and allows researchers and clinicians to effectively predict an individual pediatric patient's outcome and illness severity, with tremendous potential to improve clinical research and clinical management. PERSEVERE can predict outcome risks (favorable or unfavorable) for individual pediatric patients, within the first 24 hours of presentation with septic shock; stratification of patients presenting with septic shock outside of the first 24 hours is more challenging due to the inherently acute symptoms of septic shock. PERSEVERE has proven to be effective in derivation and test cohorts. PERSEVERE can be used to augment population-based risk scores, such as APACHE and PRISM.

The potential feasibility of a biomarker-based approach to stratification of pediatric patients early in the course of illness has been demonstrated (Wong, H. et al. Am. J. Respir. Crit. Care Med. 178:276-82 (2008)). This study demonstrated that a specific serum interleukin-8 (IL8) cut-off level, obtained within 24 hours of presentation to the pediatric intensive care unit, has a 95% negative predictive value for mortality in children with septic shock who were receiving standard care (confidence interval of 90 to 98%; likelihood ratio of 0.4 with confidence interval of 0.2 to 0.7). In contrast to the many previous studies describing measurements of cytokines and other mediators in children with septic shock (see, e.g., Wong, H. et al. Crit. Care Med. 23:835-42 (1995); Wong, H. et al. J. Ped. Infect. Dis. 14:1087-91 (1995); Wheeler, D. et al. Ped. Crit. Care Med. 6:308-11 (2005); Wheeler, D. et al. Inflamm. Res. 56:216-9 (2007); Giuliano, Jr., J. et al. Shock 28:650-4 (2007); Wheeler, D. et al. Crit. Care Med. 36:1297-1303 (2008); Kaplan, J. et al. Intensive Care Med. 36:123-30 (2010); Nowak, J. et al. Ped. Crit. Care Med. 11:213-6 (2010)), these IL8 data were prospectively validated across two independent, large test cohorts of children with septic shock.

Based on these data, the use of IL8 alone to exclude pediatric patients from septic shock interventional clinical trials that carry more than minimal risk has been exploited to generate a predictive model. This model performs better than PRISM; however, despite an excellent negative predictive value, the positive predictive value of the IL8 cut-off was lacking, meaning that considering IL8 in isolation does not sufficiently discriminate between patients who are likely to survive and those who are not; sensitivity and specificity for this model were also not very robust. As described herein, use of an expanded panel of biomarkers can maximize both negative and positive predictive capability, as has been achieved via PERSEVERE.

PERSEVERE can have an immediate and direct major impact in the field of pediatric septic shock. This model allows for more effective risk stratification of pediatric patients for the conduct of clinical trials by improving the risk to benefit ratio of a given experimental therapy by allowing for effective exclusion of pediatric patients having a high probability of survival with standard care. This approach is particularly important for experimental therapies that carry significant risks for serious adverse events, as previously demonstrated (Wong, H. et al. Am. J. Respir. Crit. Care Med. 178:276-82 (2008)). PERSEVERE also allows for the effective inclusion of pediatric patients having a high risk of mortality. This approach will be particularly important for trials having mortality as the primary outcome measure. By effectively selecting a subpopulation with a relatively high mortality risk, the sample size required for acceptable statistical power could be effectively lowered. As clinical trial expenditures increase, the need to minimize required sample size becomes increasingly important.

PERSEVERE also allows for more rational application of current and future high risk therapies for individual children with septic shock, outside of the clinical trial context. For example, high risk but potentially effective therapies, such as extracorporeal membrane oxygenation/life support, plasmapheresis, pulmonary artery catheterization, and high volume continuous hemofiltration, are widely applied as "last ditch" efforts in pediatric septic shock. PERSEVERE allows for a more objective and timely selection of pediatric patients for these high risk therapies, thus increasing the probability of success.

Program Infrastructure

The research described herein leveraged a translational research program focused on gene expression profiling in pediatric septic shock, with a robust infrastructure that can be readily leveraged. Ten major pediatric centers contributed samples and clinical data to the research program through a streamlined system for sample submission. Specifically, centers were provided with the necessary collection tubes, labels, packing materials, and prepaid overnight shipping labels to facilitate sample submission. All samples were barcoded and tracked via the Biological Specimen Tracking System (BSTS), which is web-based and was developed locally, thereby allowing for readily accessible training and troubleshooting.

An annotated clinical database called Protocol Manager was linked to the BSTS to support this translational research program. This database was developed using the local resources of the Division of Pediatric Informatics (DPI, Cincinnati Children's Hospital Medical Center, Cincinnati, Ohio) and is web-enabled such that the collaborating centers can capture and directly enter data at the local level. All DPI data collection systems incorporated a multi-layered data security approach through the use of roles, user accounts, and passwords. Secure data were protected by a firewall system. All data were stored and accessed in accordance with the internet security policy of the Health Insurance Portability and Accountability Act (HIPAA) Compliance Federation of America (HCFA) and HIPAA regulations. Data management included industry standard backup, restore, and disaster recovery methodologies.

All annotated clinical data were de-identified to conceal information in the database that directly identifies the patient (i.e. name, medical record number, address, parents, etc.). This type of information was encrypted in the database, and patients were assigned a unique research number for database queries; these research numbers were linked to samples via bar codes using the BSTS. The database was NOT de-identified with respect to disease process, outcomes, and clinical data. In fact, the database contains extensive clinical data (co-morbid conditions, medications, laboratory values, microbiology studies, outcomes, etc.), which allow biological data to be analyzed in the context of important clinical phenotypes. The database and the program's standard operating procedures were designed to ensure capture and entry of valid clinical data, with multiple strategies and cross-checks to ensure the validity of the clinical data.

Identification of Candidate Biomarkers

As described herein, microarray data (mRNA) was used to derive the candidate biomarkers (proteins). Microarray data has been previously demonstrated to be readily leveraged to a protein biomarker approach to stratify outcome risk in pediatric septic shock (Wong, H. et al. *Am. J. Respir. Crit. Care Med.* 178:276-82 (2008)).

As described herein, a list of candidate biomarker genes was selected for derivation of PERSEVERE. Rather than subjectively selecting a group of biomarker genes based on previous findings and theories, candidate biomarker genes were selected using a systematic, objective, and relatively unbiased approach. All candidate biomarkers have biological plausibility and can be readily measured.

Assigning "significance" to differentially regulated genes from a microarray experiment can be highly dependent on the filtering/statistical approach applied (Allison, D. et al. *Nat. Rev. Genet.* 7:55-56 (2006)). Accordingly, as described herein, two distinct but complementary approaches were taken to derive a list of candidate biomarker gene probes for pediatric septic shock, namely a statistics-based approach and a class prediction-based approach. These approaches were applied to an internally-developed microarray database for the unbiased selection of multiple candidate stratification biomarkers. The microarray data from which the genes were selected represent the first 24 hours of presentation to the pediatric intensive care unit.

Lists of candidate biomarker gene probes were developed from each of the statistics-based approach and class prediction-based approach and were compared to determine those genes common to the two lists. Because the resulting 117 gene list (Table 3) was derived from the overlap between the two candidate gene lists, which were in turn derived by two rigorous but distinct approaches, this gene list can serve as an unbiased and robust working list from which to select candidate biomarker genes for pediatric septic shock outcome.

The above-referenced 117 gene list (Table 3) was further refined by selecting for biomarkers with biological plausibility with regard to the pathobiology of pediatric septic shock, the host response to infection, and/or the host inflammatory response and whether the gene product (protein) can be readily measured in the blood. Based on these two criteria, a working list of 15 candidate biomarker genes was derived (Table 4).

The 15 gene probes shown in Table 4 represent the foundation for the derivation of PERSEVERE. This foundation is particularly strong, as the genes were selected in a systematic and rigorous manner, based on a combined statistical approach and a class prediction approach. The selection criteria defined a priori were that: 1) the gene product (that is, protein) must have biological and mechanistic plausibility regarding the host response to infection, immunity, and/or inflammation, and 2) the gene product must be capable of being readily measured in the serum compartment.

The selection process also had limited, if any, bias, having begun with the entire probe set on the array such that any gene could have been selected. The only potential biases were the inclusion of the definition of "biological plausibility" and the technical limitation of being able to readily measure the biomarker in the blood.

Additionally, the derivation and test cohorts represent 17 different institutions in the United States, thus taking into account any potential variability in "standard" care and thereby confirming the potential generalizability of PERSEVERE. Participant eligibility was unrestricted and enrollment was based exclusively on pediatric-specific criteria for septic shock. The only exclusion criterion was the inability to obtain informed consent. Consequently, the study cohorts represent the entire spectrum of pediatric septic shock, including patients with a broad range of significant co-morbidities typically encountered in clinical practice. In addition, the mortality rate and illness severity in this study are consistent with published studies (Watson, R. et al. *Am. J. Resp. Crit. Care Med.*, 167:695-701 (2003); Nadel, S. et al. *Lancet*, 369:836-43 (2007); Watson, R. et al. *Pediatr. Crit. Care Med.*, 6:S3-5 (2005)). Because clinical care was not under protocol, PERSEVERE appears to be independent of variability in local clinical practice patterns and nuances. These features will allow for the application of PERSEVERE in clinical practice.

Risk Model Derivation and Validation

The PERSEVERE model was then derived using 12 of the 15 genes shown in Table 4. This model allowed for the development a pediatric septic shock derivation cohort that effectively stratifies illness severity and outcome based on a biomarker profile obtained within 24 hours of admission to the pediatric intensive care unit. Because samples were obtained from over 10 different pediatric centers from across the United States, the derivation cohort provided an excellent representation of the general pediatric septic shock population.

A decision tree was then developed through a binary recursive partitioning algorithm, and 2×2 contingency tables were assembled, showing true positives, true negatives, false positives, and false negatives. This table allows for the calculation of performance characteristics, such as sensitivity, specificity, positive predictive value (PPV), negative predictive value (NPV), likelihood ratio (LR), and confidence interval (CI). This model therefore can reveal complex interactions between candidate predictor variables and eliminate poor predictor variables.

PERSEVERE was then prospectively evaluated in a separate, independent test cohort of children with septic shock. Prospective validation of a derived risk model is a standard and required approach to rigorous clinical investigations. The feasibility of prospectively validating biomarker-based risk models in the context of pediatric septic shock has been previously demonstrated (Wong, H. et al. *Am. J. Respir. Crit. Care Med.* 178:276-82 (2008)).

Validation of the performance of PERSEVERE in the test cohort can have a major positive impact on the future conduct of clinical trials targeted at the pediatric septic shock population and in the application of high risk therapies for individual children with septic shock, as previously discussed. The method of developing the PERSEVERE model can be reiterated in a larger patient cohort to develop a decision tree with additional biomarkers, branches, and/or nodes in order to further improve model performance.

Data for PERSEVERE were initially explored using descriptive statistics, box-and-whisker plots, and histograms, both overall and stratified by outcome. In addition to providing a gross overview of the data, exploration allows an additional check of data accuracy beyond those captured at the case report form level. Subsequent to data exploration, the primary analysis was conducted.

The existing cohort data set was used to derive a risk model describing the relationship between the 12 identified biomarkers, clinical data including the PRISM score, and outcomes. The model was then validated using prospectively collected data. This general approach was described for analysis of the primary outcome, 28-day mortality/survival. A similar approach was used for analysis of each of the secondary outcomes (organ failures beyond 14 and 28 days, and limb loss), with the physiologic mechanism of organ failure and limb loss potentially implicating different biomarkers for accurately predicting risk.

A risk model was then developed using a classification and regression tree (CART) analysis, which has the potential to discover complex interactions between predictor variables that are otherwise not apparent by traditional approaches. CART relies on computer algorithms that conduct multiple iterations of binary recursive partitioning. This method is binary in that it splits the patient cohort into two groups and recursive in that the splitting is repeated multiple times, such that a series of daughter nodes are generated. The splitting of the patient cohort into sections is partitioning.

For the CART analysis, 220 pediatric patients with septic shock were studied, including 23 non-survivors. All 12 stratification biomarkers were used in the modeling procedure, and age and gender were included as potential predictor variables. The target variable to predict was outcome (i.e. alive or dead at 28 days after study entry).

The "leave-X-out cross validation" option was used in the CompuMine (CompuMine, Uppsala, Sweden) analysis platform, with X=5. In this process, the algorithm removed 5 patients from the 220 patients and tried to predict their outcome based on the biomarker levels of the remaining 215 patients. This approach yielded over 40 potential models, as it can efficiently analyze multiple scenarios based on "leaving out" different sets of patients. All of the algorithm's default parameters were used, except random sampling was not allowed. The "class weighting" option was not used.

The models that were potentially reasonable to test were then selected from the over 40 potential models/classification trees generated by this approach. Any model with an area under the curve of <0.900 was eliminated, as was any model in which a given biomarker repeated along a given branch of the decision tree. These exclusion criteria yielded a set of 5 models to test.

This model was then further refined by requiring that for any given pair of terminal daughter nodes, at least one of the daughter nodes had to contain at least 11 subjects (i.e. 5% of the original root node of 220 subjects). This refinement yielded the 5-biomarker, 5-decision rule, 10-daughter node classification tree that appears in FIG. 2.

This model was replicated using the Salford Predictive Modeler (Salford Systems, San Diego, Calif.), which includes a 10-fold cross-validation procedure (analogous to leave-10-out cross-validation). Using this algorithm and the default parameters produced a similar, though not identical, model. The identical model was produced by changing the "priors" setting to "learn," meaning that the algorithm learns the frequency of the classes of interest (i.e. alive vs. dead). The default parameter treats the classes equally. The "cost matrix" of a false negative was also changed to 1.6, meaning that the algorithm was instructed that there is a higher cost associated with predicting a subject as a survivor for a subject that ultimately dies, as opposed to predicting death in someone who is an actual survivor. All terminal nodes were also required to contain at least 5 subjects.

In this way, the identical model/tree was generated using two different CART analysis platforms. The risk model was validated by "dropping" the patients in the test cohort along the derived classification tree.

Three biomarkers, namely CCL3, HSPA 1B, and IL8, were found to be the primary predictors in PERSEVERE. These three biomarkers consistently contribute to the upper level decision rules of both the initially derived tree and the subsequent updated tree. ELA2 and LCN2 contributed to predictive capacity in the initially derived tree, but not in the subsequent updated tree, which instead included GZMB, MMP8, and patient age. GZMB (Freishtat, R. et al. *Am. J. Resp. Crit. Care Med.*, 179:467-73 (2009); Sharron, M. et al. *PLoS One*, 7:e41549 (2012)) and MMP8 (Solan, P. et al. *Crit. Care Med.*, 40:379-87 (2012)) as currently being pursued as novel therapeutic targets in septic shock, and younger age was previously linked to higher mortality in pediatric septic shock (Watson, R. et al. *Am. J. Resp. Crit. Care Med.,* 167:695-701 (2003)). Including additional patients in future modeling procedures will further define the components of the lower-level decision rules.

Illness severity scores (such as PRISM) are robust for predicting the outcome of general ICU populations but are not intended for stratification and are not septic shock-specific (Vincent, J. et al. *Crit. Care Med.,* 38:283-7 (2010)). The updated PERSEVERE model was found to have a higher area under the curve than PRISM. In addition, at a comparable sensitivity of 93%, the PPV and specificity of PERSEVERE are 2-fold higher than that of PRISM.

An overall 32% PPV for mortality in the updated model may be viewed as being relatively low. However, PPV is highly influenced by prevalence and consequently needs to be interpreted in the context of prevalence [19]. In this study cohort, overall mortality was 11%. Therefore, the model identifies a cohort (namely, high-risk patients) with a mortality rate that is almost 3-fold higher than the overall cohort mortality. In addition, the model identifies a cohort (namely, low-risk patients) with an overall morality of 1%. Thus, at its most basic level, PERSEVERE divides the overall cohort into two populations having a 30-fold difference in mortality.

Use of PERSEVERE in Clinical Trial Enrollment and Clinical Research and Management The sickest patients can be identified via PERSEVERE based on the likelihood of a negative outcome, and these patients can then be selected for high risk interventions, while the low risk patients can be excluded from high risk interventions. The net result is the generation of a study population with a more favorable risk to benefit ratio. PERSEVERE can also be used to stratify pediatric septic shock patients for low risk clinical trials. The effects of the low risk intervention can be assessed post-hoc based on risk stratification. The least sick patients can be identified via the model based on the likelihood of a positive outcome, and these patients can then be selected for low risk interventions.

Accordingly, PERSEVERE can be used to select participants for interventional clinical trials. Excluding participants with very low mortality risk, while simultaneously selecting those at greatest mortality risk, increases the magnitude of possible survival benefit of a new therapy, while not placing those most likely to survive at risk of any adverse effects of a new therapeutic approach. Based on the test characteristics of the updated model, PERSEVERE has the potential to exclude patients having up to a 99% probability of survival with standard care, while including patients with up to a 32% probability of death. The latter is clinically relevant given that the best available epidemiological data indicate an overall mortality of about 10% for pediatric septic shock in the USA (Czaja, A. et al. *Pediatrics,* 123:849-57 (2009); Watson, R. et al. *Am. J. Respir. Crit. Care Med.* 167:695-701 (2003)).

The largest pediatric septic shock interventional trial to date employed a surrogate primary outcome variable because power calculations based on an assumed mortality rate of 12% would have required more than 3,000 subjects to achieve sufficient power to detect an absolute decrease in mortality of 2% (Nadel, S. et al. *Lancet* 369:836-43 (2007)). Beginning with a cohort at higher predicted risk of mortality would have allowed greater flexibility in study design, with the target of a larger absolute risk reduction, and hence a smaller sample size. By stratifying patients via PERSEVERE, one has the potential to optimize the risk-to-benefit ratio of a test agent having more than minimal risk, and consequently conduct more rational clinical trials.

PERSEVERE was developed using serum collected during the first 24 hours of admission to the PICU, which is the optimal period for initiating new therapeutic approaches, and thus for risk-stratifying patients. If PERSEVERE is not used to determine eligibility, it can be taken into account by conducting a stratified outcomes analysis.

Outside of the clinical trial context, PERSEVERE can also help inform clinical decisions regarding the application of high risk, invasive therapeutic and support modalities in septic shock, such as extracorporeal membrane oxygenation/life support, plasmapheresis, pulmonary artery catheterization, and high volume continuous hemofiltration. PERSEVERE can also serve as a benchmark for septic shock-specific quality improvement and quality assurance efforts. For example, based on the updated model, higher than 1% mortality in the lowest-risk patients can be an indicator of poor performance, while lower than 32% mortality in the highest-risk group can be indicative of good performance. Moreover, differences in illness severity in those who survived but who were predicted to die, and in those who survived and were predicted to survive, could provide some clues to tailoring treatments to improve outcomes for all pediatric septic shock patients.

PERSEVERE can also be used to make individual patient decisions at the bedside (point of care). PERSEVERE can be used to make clinical decisions given the rapid turnaround time of the analysis. The PERSEVERE panel can select the pediatric patients most likely to benefit from a particular treatment or exclude patients who are predicted to do well with standard care. While a number of unproven but potentially beneficial therapies for sepsis exist, most are invasive and carry substantial iatrogenic risks. As described herein, the panel has the potential to select the pediatric patients most likely to benefit from a particular treatment; the panel can also exclude pediatric patients who are predicted to do well with standard care.

PERSEVERE can also be used as a tool for quality improvement by serving as a metric for institutions to measure their respective outcomes in pediatric patients with septic shock. If a substantial number of these patients are actually dying, then this could serve as a trigger to examine their clinical processes. Alternatively, if an institution has a large number of high risk pediatric patients who are actually surviving, then PERSEVERE can be used to study those patients.

PERSEVERE can be periodically updated. As more patients are included into the modeling process, some of the biomarker cutoff values included in the decision trees depicted in FIGS. 6 and 8 can change. In addition, new biomarkers can be identified that can contribute to the decision tree, or the previously tested biomarkers might be useful for refining the risk stratification, or additional patient information can be incorporated into the decision tree or used in combination with the decision tree. Such changes can enhance predictive performance and further increase generalizability of the decision tree.

Certain embodiments of the invention include using quantification data from a gene-expression analysis and/or from an mRNA analysis, from a sample of blood, urine, saliva, or the like. Embodiments of the invention include not only methods of conducting and interpreting such tests but also include reagents, kits, assays, and the like, for conducting the tests.

In an exemplary embodiment, the outcome risk stratification method is carried out on a patient to predict an outcome for a pediatric patient with septic shock. A serum sample is obtained from a pediatric patient. Serum concentrations of CCL3, HSPA1B, IL8, ELA2, and LCN2 are then measured (e.g. using a magnetic bead multi-plex platform and a Luminex® 100/200 System). The results are then used in order to predict an outcome for a pediatric patient with septic shock.

In another exemplary embodiment, serum concentrations of CCL3, HSPA1B, IL8, GZMB, and MMP8 are measured (e.g. using a magnetic bead multi-plex platform and a Luminex® 100/200 System), and the patient's age is noted. The results from the serum concentrations of CCL3, HSPA1B, IL8, GZMB, and MMP8 concentration and the patient's age are then used in combination in order to predict an outcome for a pediatric patient with septic shock.

Figure 2:
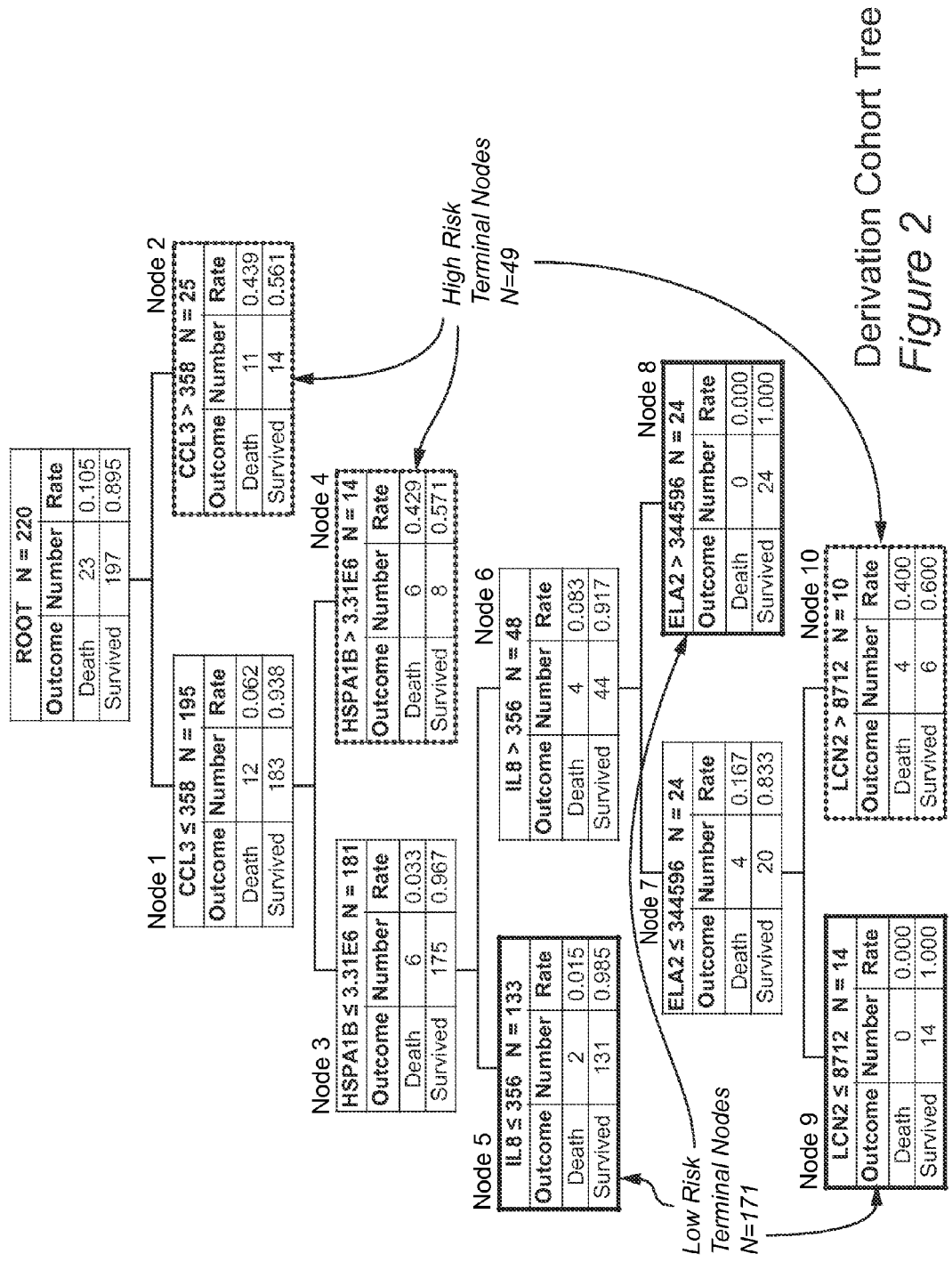
FIG. 2 depicts the classification tree for the derivation cohort. The classification tree was generated using 220 pediatric patients with septic shock, 12 candidate stratification biomarkers, and classification and regression tree (CART) analysis. CART analysis is based on a binary recursive partitioning algorithm and allows for the discovery of complex predictor variable interactions that may not be apparent with more traditional methods, such as multiple linear regression. It also has the ability to eliminate predictor variables with poor performance.

Use of the decision tree depicted in FIG. 2 in order to predict an outcome for a pediatric patient with septic shock is another exemplary embodiment of the invention. Use of the decision tree depicted in FIG. 8 in order to predict an outcome for a pediatric patient with septic shock is another exemplary embodiment of the invention.

In some embodiments, a pediatric patient with septic shock evaluated via the outcome risk stratification method described herein by subjecting the patient to the decision tree depicted in FIG. 2 or FIG. 8. In some embodiments, a patient that ends up in one of the low risk terminal nodes of the decision tree is determined to have a mortality probability ranging from 0% to 18%. In some embodiments, a patient that ends up in one of the low risk terminal nodes of the decision tree is determined to have a mortality probability of 0%, 1%, 2%, 3%, 4%, 5%, 6%, 7%, 8%, 9%, 10%, 11%, 12%, 13%, 14%, 15%, 16%, or 17%. In some embodiments, a patient that ends up in one of the high risk nodes of the decision tree is determined to have a mortality probability ranging from 18% to 40%. In some embodiments, a patient that ends up in one of the low risk terminal nodes of the decision tree is determined to have a mortality probability of 18%, 19%, 20%, 21%, 22%, 23%, 24%, 25%, 26%, 27%, 28%, 29%, 30%, 31%, 32%, 33%, 34%, 35%, 36%, 37%, 38%, or 39%. In some embodiments, a patient that ends up in one of the high risk nodes of the decision tree is determined to have a mortality probability ranging from 40% to 100%. In some embodiments, a patient that ends up in one of the low risk terminal nodes of the decision tree is determined to have a mortality probability of 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, any patient that is not considered to be low risk can be classified as high risk, i.e. a patient that is considered be to moderate risk or moderate-high risk can be classified as high risk.

Sample Size Considerations

When estimating power or sample size for multi-variable logistic regression models, it is necessary to specify the covariance matrix. Given the number of variables, the largely exploratory nature of the modeling process, and the need to determine variable groupings as a part of the analysis, it is not feasible to determine an exact sample size. Nonetheless, it is important to consider the magnitude of effect sizes that might be detected with these analyses.

There were 220 cases for derivation and 135 cases in the test cohort. The percentage of deaths in 28 days was expected to be about 15. If the prevalence of events is about 12.5%, then an odds ratio of about 2 can be detected, with the detectable odds ratio decreasing (or increasing below 1) as the prevalence increases.

A previous study using a single biomarker strategy (interleukin-8) demonstrated that patients having an interleukin-8 level >220 pg/ml (n=178), within 24 hours of admission to the PICU, had a mortality odds ratio of 4.6 (95% confidence intervals 2.1 to 10.2) (Wong, H. et al. *Am. J. Respir. Crit. Care Med.* 178:276-82 (2008)). In contrast, patients having an interleukin-8 level ≤220 pg/ml (n=154) had a mortality odds ratio of 0.2 (95% confidence intervals 0.1 to 0.4). Thus, assuming that a multi-biomarker-based risk profile will be more robust than a single biomarker-based approach, a test cohort of 200 patients provides sufficient power to validate PERSEVERE.

Sample Acquisition

Stratification of patients presenting with septic shock becomes increasingly difficult as time progresses due to the inherently acute symptoms of septic shock. Accordingly, the methods described herein which allow for stratification of individual pediatric patients in order to determine the patient's outcome risk involve acquiring a sample from a pediatric patient early in the patient's course of diagnosis and treatment.

In some embodiments, a sample is acquired from a pediatric patient within the first 60 minutes of presentation with septic shock. In some embodiments, a sample is acquired from a pediatric patient within the first 8 hours of presentation with septic shock. In some embodiments, a sample is acquired from a pediatric patient within the first 24 hours of presentation with septic shock. In some embodiments, a sample is acquired from a pediatric patient within the first 48 hours of presentation with septic shock. In some embodiments, a sample is acquired from a pediatric patient within the first 72 hours of presentation with septic shock.

In some embodiments, a sample is acquired from a pediatric patient within the first 1, 2, 3, 4, 5, 6, 7, 8, 9, or 10 hours of presentation with septic shock. In some embodiments, a sample is acquired from a pediatric patient within the first 11, 12, 13, 14, 15, 16, 17, 18, 19, or 20 hours of presentation with septic shock. In some embodiments, a sample is acquired from a pediatric patient within the first 21, 22, 23, 24, 25, 26, 27, 28, 29, or 30 hours of presentation with septic shock. In some embodiments, a sample is acquired from a pediatric patient within the first 31, 32, 33, 34, 35, 36, 37, 38, 39, or 40 hours of presentation with septic shock. In some embodiments, a sample is acquired from a pediatric patient within the first 41, 42, 43, 44, 45, 46, 47, 48, 49, or 50 hours of presentation with septic shock. In some embodiments, a sample is acquired from a pediatric patient within the first 51, 52, 53, 54, 55, 56, 57, 58, 59, or 60 hours of presentation with septic shock. In some embodiments, a sample is acquired from a pediatric patient within the first 61, 62, 63, 64, 65, 66, 67, 68, 69, or 70 hours of presentation with septic shock. In some embodiments, a sample is acquired from a pediatric patient within the first 71, 72, 73, 74, 75, 76, 77, 78, 79, or 80 hours of presentation with septic shock.

Additional Patient Information

The demographic data, clinical characteristics, and/or results from other tests or indicia of septic shock specific to a pediatric patient with septic shock can affect the patient's outcome risk. Accordingly, such demographic data, clinical characteristics, and/or results from other tests or indicia of septic shock can be incorporated into the methods described herein which allow for stratification of individual pediatric patients in order to determine the patient's outcome risk. Such demographic data, clinical characteristics, and/or results from other tests or indicia of septic shock can also be used in combination with the methods described herein which allow for stratification of individual pediatric patients in order to determine the patient's outcome risk.

Such pediatric patient demographic data can include, for example, the patient's age, race, gender, and the like.

In some embodiments, the biomarker-based risk stratification model described herein can incorporate the patient's age to determine an outcome risk. In some embodiments, the biomarker-based risk stratification model described herein can incorporate the patient's race to determine an outcome risk. In some embodiments, the biomarker-based risk stratification model described herein can incorporate the patient's gender to determine an outcome risk.

In some embodiments, the biomarker-based risk stratification model described herein can be used in combination with the patient's age to determine an outcome risk. In some embodiments, the biomarker-based risk stratification model described herein can be used in combination with the patient's race to determine an outcome risk. In some embodiments, the biomarker-based risk stratification model described herein can be used in combination with the patient's gender to determine an outcome risk.

Such patient clinical characteristics and/or results from other tests or indicia of septic shock can include, for example, the patient's co-mobidities and/or septic shock causative organism, and the like.

Patient co-morbidities can include, for example, acute lymphocytic leukemia, acute myeloid leukemia, aplastic anemia, atrial and ventricular septal defects, bone marrow transplantation, caustic ingestion, chronic granulomatous disease, chronic hepatic failure, chronic lung disease, chronic lymphopenia, chronic obstructive pulmonary disease (COPD), congestive heart failure (NYHA Class IV CHF), Cri du Chat syndrome, cyclic neutropenia, developmental delay, diabetes, DiGeorge syndrome, Down syndrome, drowning, end stage renal disease, glycogen storage disease type 1, hematologic or metastatic solid organ malignancy, hemophagocytic lymphohistiocytosis, hepatoblastoma, heterotaxy, hydrocephalus, hypoplastic left heart syndrome, IPEX Syndrome, kidney transplant, Langerhans cell histiocytosis, liver and bowel transplant, liver failure, liver transplant, medulloblastoma, metaleukodystrophy, mitochondrial disorder, multiple congenital anomalies, multi-visceral transplant, nephrotic syndrome, neuroblastoma, neuromuscular disorder, obstructed pulmonary veins, Pallister Killian syndrome, Prader-Willi syndrome, requirement for chronic dialysis, requirement for chronic steroids, retinoblastoma, rhabdomyosarcoma, rhabdosarcoma, sarcoma, seizure disorder, severe combined immune deficiency, short gut syndrome, sickle cell disease, sleep apnea, small bowel transplant, subglottic stenosis, tracheal stenosis, traumatic brain injury, trisomy 18, type 1 diabetes mellitus, unspecified brain tumor, unspecified congenital heart disease, unspecified leukemia, VATER Syndrom, Wilms tumor, and the like. Any one or more of the above patient co-morbidities can be indicative of the presence or absence of chronic disease in the patient.

Septic shock causative organisms can include, for example, *Acinetobacter baumannii*, Adenovirus, *Bacteroides* species, *Candida* species, *Capnotyophaga jenuni*, Cytomegalovirus, *Enterobacter cloacae, Enterococcus faecalis, Escherichia coli*, Herpes simplex virus, Human metapneumovirus, Influenza A, *Klebsiella pneumonia, Micrococcus* species, mixed bacterial infection, *Moraxella catarrhalis, Neisseria meningitides*, Parainfluenza, *Pseudomonas* species, *Serratia marcescens, Staphylococcus aureus, Streptococcus agalactiae, Streptococcus milleri, Streptococcus pneumonia, Streptococcus pyogenes*, unspecified gram negative rods, unspecified gram positive cocci, and the like.

In some embodiments, the biomarker-based risk stratification model described herein can incorporate the patient's co-morbidities to determine an outcome risk. In some embodiments, the biomarker-based risk stratification model described herein can incorporate the patient's septic shock causative organism to determine an outcome risk.

In some embodiments, the biomarker-based risk stratification model described herein can be used in combination with the patient's co-morbidities to determine an outcome risk. In some embodiments, the biomarker-based risk stratification model described herein can be used in combination with the patient's septic shock causative organism to determine an outcome risk.

Population-Based Risk Scores

A number of models that generate mortality prediction scores based on physiological variables have been developed to date. These can include the APACHE, PRISM, Pediatric Index of Mortality (PIM), and/pediatric logistic organ dysfunction (PELOD) models, and the like. The APACHE model considered can be APACHE I, APACHE II, APACHE III, APACHE IV, or a subsequent iteration of APACHE.

Such models can be very effective for estimating population-based outcome risks but are not intended for stratification of individual patients. The methods described herein which allow for stratification of individual patients can be used alone or in combination with one or more existing population-based risk scores.

In some embodiments, the biomarker-based risk stratification model described herein can be used with one or more additional population-based risk scores. In some embodiments, the biomarker-based risk stratification model described herein can be used in combination with APACHE. In some embodiments, the biomarker-based risk stratification model described herein can be used in combination with PRISM. In some embodiments, the biomarker-based risk stratification model described herein can be used in combination with PIM. In some embodiments, the biomarker-based risk stratification model described herein can be used in combination with PELOD. In some embodiments, the biomarker-based risk stratification model described herein can be used in combination with a population-based risk score other than APACHE, PRISM, PELOD, and PRISM.

High Risk Therapies

High risk, invasive therapeutic and support modalities can be used to treat septic shock. The methods described herein which allow for stratification of individual pediatric patients in order to determine the patient's outcome risk can help inform clinical decisions regarding the application of high risk therapies to specific pediatric patients, based on the patient's outcome risk.

High risk therapies include, for example, extracorporeal membrane oxygenation/life support, plasmapheresis, pulmonary artery catheterization, high volume continuous hemofiltration, and the like.

In some embodiments, individualized treatment can be provided to a pediatric patient by selecting a pediatric patient classified as high risk by the methods described herein for one or more high risk therapies. In some embodiments, individualized treatment can be provided to a pediatric patient by excluding a pediatric patient classified as low risk from one or more high risk therapies.

Certain embodiments of the invention include using quantification data from a gene-expression analysis and/or from a mRNA analysis, from a sample of blood, urine, saliva, broncho-alveolar lavage fluid, or the like. Embodiments of the invention include not only methods of conducting and interpreting such tests but also include reagents, kits, assays, and the like, for conducting the tests.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of subjects with a positive test result who are correctly diagnosed; for tests with a high PPV, a positive test indicates the presence of the condition in question. The NPV of a particular diagnostic test represents the proportion of subjects with a negative test result who are correctly diagnosed; for tests with a high NPV, a negative test indicates the absence of the condition. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnosis based upon subjecting a patient to the decision tree described herein in order to predict an outcome for a pediatric patient with septic shock.

The correlations disclosed herein, between pediatric patient septic shock biomarker levels and/or mRNA levels and/or gene expression levels, provide a basis for conducting a diagnosis of septic shock, or for conducting a stratification of patients with septic shock, or for enhancing the reliability of a diagnosis of septic shock by combining the results of a quantification of a septic shock biomarker with results from other tests or indicia of septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Derivation of Candidate Biomarker Genes to Predict Outcome in Pediatric Septic Shock Compilation of Complete Set of Potential Biomarker Candidates Biomarker candidates were derived from genome-wide microarray expression data developed from studying children with septic shock through an NIH-supported translational research program (Wong, H. et al. *Crit. Care Med.* 178:276-82 (2009); Wong, H. et al. *Physiol. Genomics* 30:146-55 (2007); Wong, H. *Pharmacogenomics* 8:1287-90 (2007); Shanley, T. et al. *Mol. Med.* 13:495-508 (2007); Cvijanovich, N. et al. *Physiol. Genomics* 34:127-34 (2008)). Complete microarray data was analyzed on a Human Genome U133 Plus 2.0 GeneChip (Affymetrix, Santa Clara, Calif.) from whole blood-derived RNA using a PaxGene Blood RNA Kit (Qiagen, Venlo, Netherlands).

Data were obtained from 98 children with septic shock. All data were derived from RNA samples obtained within 24 hours of admission to the pediatric intensive care unit and were complemented by parallel serum samples and extensive annotated clinical data. There were 17 non-survivors in this cohort as defined by 28-day outcome. All microarray data initially underwent robust multiple-array average normalization, followed by normalization to the median values of normal control samples (n=32), as previously published (Wong, H. et al. *Crit. Care Med.* 178:276-82 (2009); Wong, H. et al. *Physiol. Genomics* 30:146-55 (2007); Shanley, T. et al. *Mol. Med.* 13:495-508 (2007); Cvijanovich, N. et al. *Physiol. Genomics* 34:127-34 (2008)). All data are compliant with Minimum Information About a Microarray Experiment (MIAME) standards and have been deposited in the Gene Expression Omnibus (found at http <colon slash slash> www <dot> ncbi <dot> nlm <dot> nih <dot> gov <slash> geo) under accession number GSE13904.

This microarray database was then leveraged for the unbiased selection of multiple candidate stratification biomarkers. From these data, two distinct but complementary approaches were taken to derive a list of candidate biomarker genes for pediatric septic shock, namely a statistics-based approach and a class prediction-based approach.

Statistics-Based Approach to Determine Biomarker Candidates

A statistics-based approach was developed to determine a more refined list of biomarker candidates. A 3-group analysis of variance (ANOVA) was performed for all 87,933 gene probes on the microarray, using controls, septic shock survivors, and septic shock non-survivors as the comparison groups. The ANOVA consisted of a Welch test with correction for multiple comparisons via a Benjamini-Hochberg False Discovery Rate of 5%, which yielded >20,000 differentially regulated gene probes between the three comparison groups.

A post-hoc Student-Newman-Keuls test was then performed to determine the specific inter-group differences in gene expression. This post-hoc test yielded 137 candidate biomarker gene probes that were differentially regulated between septic shock survivors and non-survivors.

Class Prediction-Based Approach to Determine Biomarker Candidates

A class prediction-based approach was also developed to determine a more refined list of biomarker candidates in parallel with the statistics-based approach, and a Support Vector Machines-based dichotomous class prediction modeling was applied to identify candidate biomarker genes. All 87,933 gene probes on the array were studied to attempt to predict "survivor" and "non-survivor" classes via leave-one-out cross validation modeling. This class prediction modeling approach was able to correctly predict survival or non-survival in 84 of the 98 patients (86% correct class prediction); specifically, the model correctly predicted 15 of the 17 non-survivors (88%) and 69 of the 81 survivors (85%).

The Fisher test was then used for gene selection. The top 5% class predictor gene probes were extracted from the starting 87,933 gene probes to yield 4,397 candidate biomarker gene probes of interest.

Further Refinement of Candidate Biomarkers

Having derived candidate biomarker gene probe lists by two distinct methods, namely the statistics-based approach and the class prediction-based approach, a Venn analysis was then conducted to determine which genes are common to the two gene lists. As shown in FIG. 1, 117 candidate biomarker gene probes were found to be common to the gene lists developed through the statistics-based and class prediction-based approaches (Table 1). Because this list of 117 candidate biomarker gene probes was derived from the overlap between the two candidate gene probe lists, which were in turn derived by two rigorous but distinct approaches, this gene probe list can serve as an unbiased and robust working list from which to select candidate biomarker genes for pediatric septic shock outcome.

TABLE 1

List of 117 candidate biomarker gene probes common to statistics-based approach and class prediction-based approach.

| Affymetrix ID | Gene Symbol | Description |
|---|---|---|
| 222608_s_at | ANLN | anillin, actin binding protein |
| 202888_s_at | ANPEP | alanyl (membrane) aminopeptidase |
| 223484_at | C15orf48 | chromosome 15 open reading frame 48 |
| 1553920_at | C9orf84 | chromosome 9 open reading frame 84 |
| 1554786_at | CASS4 | Cas scaffolding protein family member 4 |
| 204103_at | CCL4 | chemokine (C-C motif) ligand 4 |
| 214710_s_at | CCNB1 | cyclin B1 |
| 202705_at | CCNB2 | cyclin B2 |
| 266_s_at | CD24 | CD24 molecule |
| 209771_x_at | CD24 | CD24 molecule |
| 203799_at | CD302 | CD302 molecule |
| 209795_at | CD69 | CD69 molecule |
| 210895_s_at | CD86 | CD86 molecule |
| 210559_s_at | CDC2 | cell division cycle 2, G1 to S and G2 to M |
| 206676_at | CEACAM8 | carcinoembryonic antigen-related cell adhesion molecule 8 |
| 218542_at | CEP55 | centrosomal protein 55 kDa |
| 204170_s_at | CKS2 | CDC28 protein kinase regulatory subunit 2 |
| 219890_at | CLEC5A | C-type lectin domain family 5, member A |
| 221698_s_at | CLEC7A | C-type lectin domain family 7, member A |
| 208146_s_at | CPVL | carboxypeptidase, vitellogenic-like |
| 205931_s_at | CREB5 | cAMP responsive element binding protein 5 |
| 205898_at | CX3CR1 | chemokine (C-X3-C motif) receptor 1 |
| 1568934_at | CX3CR1 | chemokine (C-X3-C motif) receptor 1 |
| 202887_s_at | DDIT4 | DNA-damage-inducible transcript 4 |
| 205000_at | DDX3Y | DEAD (Asp-Glu-Ala-Asp) box polypeptide 3, Y-linked |
| 224327_s_at | DGAT2 | diacylglycerol O-acyltransferase homolog 2 (mouse) |
| 231886_at | DKFZP434B2016 | similar to hypothetical protein LOC284701 |
| 235341_at | DNAJC3 | DnaJ (Hsp40) homolog, subfamily C, member 3 |
| 206871_at | ELA2 | elastase 2, neutrophil |
| 210724_at | EMR3 | egf-like module containing, mucin-like, hormone receptor-like 3 |
| 231029_at | F5 | coagulation factor V (proaccelerin, labile factor) |
| 202345_s_at | FABP5/<br>FABP5L2/<br>FABP5L7 | fatty acid binding protein 5 (psoriasis-associated)/<br>fatty acid binding protein 5-like 2/<br>fatty acid binding protein 5-like 7 |
| 204834_at | FGL2 | fibrinogen-like 2 |
| 227265_at | FGL2 | fibrinogen-like 2 |
| 220326_s_at | FLJ10357 | hypothetical protein FLJ10357 |
| 241627_x_at | FLJ10357 | hypothetical protein FLJ10357 |
| 58780_s_at | FLJ10357 | hypothetical protein FLJ10357 |
| 204072_s_at | FRY | furry homolog (Drosophila) |
| 224148_at | FYB | FYN binding protein (FYB-120/130) |
| 213524_s_at | G0S2 | G0/G1switch 2 |
| 204222_s_at | GLIPR1 | GLI pathogenesis-related 1 |
| 207651_at | GPR171 | G protein-coupled receptor 171 |
| 228949_at | GPR177 | G protein-coupled receptor 177 |
| 210164_at | GZMB | granzyme B (granzyme 2, cytotoxic T-lymphocyte-associated serine esterase 1) |
| 206643_at | HAL | histidine ammonia-lyase |
| 202581_at | HSPA1A/<br>HSPA1B | heat shock 70 kDa protein 1A/<br>heat shock 70 kDa protein 1B |
| 206976_s_at | HSPH1 | heat shock 105 kDa/110 kDa protein 1 |
| 208200_at | IL1A | interleukin 1, alpha |
| 211506_s_at | IL8 | interleukin 8 |
| 206700_s_at | JARID1D | jumonji, AT rich interactive domain 1D |
| 204444_at | KIF11 | kinesin family member 11 |
| 224534_at | KREMEN1 | kringle containing transmembrane protein 1 |
| 218963_s_at | KRT23 | keratin 23 (histone deacetylase inducible) |
| 212531_at | LCN2 | lipocalin 2 |

TABLE 1-continued

List of 117 candidate biomarker gene probes common to statistics-based approach and class prediction-based approach.

| Affymetrix ID | Gene Symbol | Description |
|---|---|---|
| 1558920_at | LOC100128590 | hypothetical protein LOC100128590 |
| 230292_at | LOC100131993 | Similar to hCG2020760 |
| 201909_at | LOC100133662/ RPS4Y1 | hypothetical protein LOC100133662/ ribosomal protein S4, Y-linked 1 |
| 1558882_at | LOC401233 | similar to HIV TAT specific factor 1; cofactor required for Tat activation of HIV-1 transcription |
| 244065_at | LOC643827 | similar to cell recognition molecule CASPR3 |
| 205114_s_at | LOC728830/ CCL3L1/ CCL3/ CCL3L3 | chemokine (C-C motif) ligand 3/ chemokine (C-C motif) ligand 3-like 1/ chemokine (C-C motif) ligand 3-like 3/ similar to C-C motif chemokine 3-like 1 precursor (Small-inducible cytokine A3-like 1) (Tonsillar lymphocyte LD78 beta protein) (LD78-beta(1-70)) (G0/G1 switch regulatory protein 19-2)(G0S19-2 protein) (PAT 464.2) |
| 205114_s_at | LOC728830/ CCL3L1/ CCL3/ CCL3L3 | chemokine (C-C motif) ligand 3/ chemokine (C-C motif) ligand 3-like 1/ chemokine (C-C motif) ligand 3-like 3/ similar to C-C motif chemokine 3-like 1 precursor (Small-inducible cytokine A3-like 1) (Tonsillar lymphocyte LD78 beta protein) (LD78-beta(1-70)) (G0/G1 switch regulatory protein 19-2) (G0S19-2 protein) (PAT 464.2) |
| 202018_s_at | LTF | lactotransferrin |
| 36711_at | MAFF | v-maf musculoaponeurotic fibrosarcoma oncogene homolog F (avian) |
| 220945_x_at | MANSC1 | MANSC domain containing 1 |
| 210484_s_at | MGC31957/ TNFRSF10C | hypothetical protein MGC31957/ tumor necrosis factor receptor superfamily, member 10c, decoy without an intracellular domain |
| 203435_s_at | MME | membrane metallo-endopeptidase |
| 203434_s_at | MME | membrane metallo-endopeptidase |
| 231688_at | MMP8 | matrix metallopeptidase 8 (neutrophil collagenase) |
| 207329_at | MMP8 | matrix metallopeptidase 8 (neutrophil collagenase) |
| 217546_at | MT1M | metallothionein 1M |
| 204162_at | NDC80 | NDC80 homolog, kinetochore complex component (*S. cerevisiae*) |
| 213915_at | NKG7 | natural killer cell group 7 sequence |
| 236930_at | NUMB | Numb homolog (*Drosophila*) |
| 218039_at | NUSAP1 | nucleolar and spindle associated protein 1 |
| 205041_s_at | ORM1/ ORM2 | orosomucoid 1/ orosomucoid 2 |
| 206470_at | PLXNC1 | plexin C1 |
| 218009_s_at | PRC1 | protein regulator of cytokinesis 1 |
| 242482_at | PRKAR1A | protein kinase, cAMP-dependent, regulatory, type I, alpha (tissue specific extinguisher 1) |
| 220570_at | RETN | resistin |
| 216834_at | RGS1 | regulator of G-protein signaling 1 |
| 202388_at | RGS2 | regulator of G-protein signaling 2, 24 kDa |
| 230720_at | RNF182 | ring finger protein 182 |
| 204669_s_at | RNF24 | ring finger protein 24 |
| 209267_s_at | SLC39A8 | solute carrier family 39 (zinc transporter), member 8 |
| 1556583_a_at | SLC8A1 | solute carrier family 8 (sodium/calcium exchanger), member 1 |
| 224724_at | SULF2 | sulfatase 2 |
| 201506_at | TGFBI | transforming growth factor, beta-induced, 68 kDa |
| 201109_s_at | THBS1 | thrombospondin 1 |
| 201110_s_at | THBS1 | thrombospondin 1 |
| 211163_s_at | TNFRSF10C | tumor necrosis factor receptor superfamily, member 10c, decoy without an intracellular domain |
| 206222_at | TNFRSF10C | tumor necrosis factor receptor superfamily, member 10c, decoy without an intracellular domain |
| 201292_at | TOP2A | topoisomerase (DNA) II alpha 170 kDa |
| 201291_s_at | TOP2A | topoisomerase (DNA) II alpha 170 kDa |
| 204822_at | TTK | TTK protein kinase |
| 202589_at | TYMS | thymidylate synthetase |
| 228492_at | USP9Y/ LOC100130216 | hypothetical protein LOC100130216/ ubiquitin specific peptidase 9, Y-linked (fat facets-like, *Drosophila*) |
| 204026_s_at | ZWINT | ZW10 interactor |
| 236552_at | N/A | N/A |
| 1561654_at | N/A | N/A |
| 243170_at | N/A | N/A |
| 232555_at | N/A | N/A |
| 1556923_at | N/A | N/A |
| 244218_at | N/A | N/A |
| 239102_s_at | N/A | N/A |
| 238170_at | N/A | N/A |
| 241041_at | N/A | N/A |
| 1570194_x_at | N/A | N/A |
| 217521_at | N/A | N/A |
| 239021_at | N/A | N/A |
| 227618_at | N/A | N/A |
| 239464_at | N/A | N/A |

TABLE 1-continued

List of 117 candidate biomarker gene probes common to statistics-based approach and class prediction-based approach.

| Affymetrix ID | Gene Symbol | Description |
|---|---|---|
| 1566964_at | N/A | N/A |
| 232958_at | N/A | N/A |
| 230585_at | N/A | N/A |
| 216782_at | N/A | N/A |
| 234640_x_at | N/A | N/A |
| 234632_x_at | N/A | N/A |

Final Selection of Candidate Biomarker Gene List

To derive a final list of candidate biomarker genes, the above-referenced 117 gene probe list (Table 3) was then examined for genes meeting two simultaneous a priori criteria: 1) the gene has a reasonable level of biological plausibility with regard to the pathobiology of pediatric septic shock, the host response to infection, and/or the host inflammatory response; and 2) the gene product (protein) can readily be feasibly measured in the serum. Based on these two criteria, a final working list of 15 candidate biomarker genes was derived, as shown in Table 2. Enzyme-linked immunosorbent assay (ELISA)- and/or multiplex-based platforms are commercially available for detection of each of these gene products in the serum.

TABLE 2

Final working list of 15 candidate biomarker gene probes.

| Gene Symbol | Description | Fold Induction* |
|---|---|---|
| CCL3 | C-C chemokine ligand 3; a.k.a. MIP-1α | 2.8 |
| LCN2 | Lipocalin 2; a.k.a. NGAL | 2.7 |
| MMP8 | Matrix metallopeptidase 8; a.k.a. neutrophils collagenase | 2.6 |
| RETN | Resistin | 2.4 |
| THBS | Thrombospondin 1 | 2.2 |
| GZMB | Granzyme B | 2.2 |
| HSPA1B | Heat shock protein 70 kDa 1B | 2.1 |
| ORM1 | Orosomucoid 1, acute phase protein with unknown function | 2 |
| CCL4 | C-C chemokine ligand 3; a.k.a. MIP-1β | 1.9 |
| IL8 | Interleukin-8 | 1.8 |
| LTF | Lactotransferrin | 1.8 |
| ELA2 | Neutrophil elastase 1 | 1.8 |
| IL1A | Interleukin 1α | 0.5 |
| SULF2 | Sulfatase 2; extracellular modulator of heparan sulfate proteoglycans | 0.5 |
| FGL2 | Fibrinogen-like 2; acute phase protein similar to fibrinogen | 0.5 |

*Median of non-survivors relative to median of survivors.

Example 2

Derivation of Persevere

In a subsequent study, a multi-biomarker-based risk model (PERSEVERE) was then derived by applying the gene probe list described in Example 1 to a derivation cohort of children with septic shock. This risk model was designed to predict individual patient outcome and illness severity in pediatric septic shock.

Genomics of Pediatric Septic Shock Database

The Genomics of Pediatric Septic Shock (GPSS) database was used to generate the training and test data sets. The GPSS database has been previously described in detail (Wong, H. et al. *Physiol. Genomics* 30:146-55 (2007); Shanley, T. et al. *Mol. Med.* 13:495-508 (2007); Wong, H. *Pharmacogenomics* 8:1287-90 (2007)).

This non-interventional database supports a translational research program focused on genome-level microarray-based expression profiles of children with septic shock. Eighteen pediatric intensive care units (PICUs) in the United States have contributed samples to the GPSS. The database contains extensive clinical data, RNA samples, and concomitant serum samples. RNA and serum samples were collected within 24 hours of admission to the PICU and 48 hours after the initial sample collection; however, only serum samples drawn within 24 hours of admission to the PICU were used.

Patients

The subjects enrolled in the GPSS database included children (<11 years of age) admitted to the PICUs of multiple institutions and having a diagnosis of septic shock. Septic shock was defined based on published, pediatric-specific criteria (Goldstein, B. et al. *Pediatr. Crit. Care Med.* 6:2-8 (2005)). Full-term neonates (that is, <28 days of age) re-admitted to the hospital for septic shock were included. Clinical care was not directed by the study, and, except for when informed consent could not be obtained, no child was excluded.

After informed consent was obtained from parents or legal guardians, and within 24 hours of admission to the PICU, serum samples were obtained. Annotated clinical and laboratory data were collected daily while the participant was in the PICU. Illness severity was prospectively calculated using the pediatric risk of mortality (PRISM) score (Pollack, M. et al. *J. Pediatr.*, 131:575-81 (1997)). The number of organ failures during the initial 7 days of PICU admission was recorded using pediatric-specific criteria (Goldstein, B. et al. *Pediatr. Grit. Care Med.* 6:2-8 (2005)). PICU-free days were calculated by subtracting the actual PICU length of stay (LOS) from a theoretical maximum PICU LOS of 28 days. Patients with a PICU LOS greater than 28 days were classified as having zero PICU-free days. The primary outcome variable was all-cause 28-day mortality.

The restriction to patients ≤10 years of age reflects the specific intent to study a population strictly composed of "children," as has been done previously with the genomic data base and derivation cohort. Patients within this age group will universally be pre-pubertal, thereby excluding the adolescent age range that more approximates the adult population.

This study was conducted on 220 patients with septic shock; there were 23 non-survivors. The mortality rate of this cohort (10%) is consistent with reported epidemiology for the United States (Watson, R. et al. *Am. J. Respir. Crit. Care Med.* 167:695-701 (2003)). All patients had serum samples taken during the first 24 hours of presentation to the pediatric intensive care unit. All serum samples were extensively annotated with clinical data.

Serum Protein Biomarker Assays

Of the 15 candidate biomarker gene probes listed in Table 2, 12 biomarker gene probes were measured from patient serum samples, as listed in Table 3. The 12 candidate biomarkers (gene symbols) included: C—C chemokine ligand 3 (CCL3), C—C chemokine ligand 4 (CCL4), neutrophil elastase 2 (ELA2), granzyme B (GZMB), heat shock protein 70 kDa 1B (HSPA1B), interleukin 1α (IL1A), interleukin 8 (IL8), lipocalin 2 (LCN2), lactotransferrin (LTF), matrix metalloproteinase 8 (MMP8), resistin (RETN), and thrombospondin 1 (THBS1). These 12 biomarker gene probes were selected because 3 of the candidate biomarker gene probes, namely sulfatase 2 (SULF2), fibrinogen-like 2 (FGL2), and orosomucoid 1 (ORM1), proved difficult to incorporate into the panel.

Assays for the 12 candidate stratifcation biomarkers (see Table 5) were performed using a Luminex 200 multi-plex instrument (Luminex Corporation, Austin, Tex.) and antibody-coated magnetic beads (Millipore, Billerica, Mass.), per the manufacturer's specifications. This platform allowed for simultaneous measurements of multiple biomarkers from relatively small sample sizes; this was necessary due to the relatively limited volumes of blood samples inherent to pediatric-related clinical studies. Standard ELISA-based assays were available for all of the biomarkers of interest.

TABLE 3

List of 12 biomarker gene probes selected for panel.

| Gene Symbol | Description |
|---|---|
| CCL3 | C-C chemokine ligand 3; a.k.a. MIP-1α |
| LCN2 | Lipocalin 2; a.k.a. NGAL |
| MMP8 | Matrix metallopeptidase 8; a.k.a. neutrophils collagenase |
| RETN | Resistin |
| THBS | Thrombospondin 1 |
| GZMB | Granzyme B |
| HSPA1B | Heat shock protein 70 kDa 1B |
| CCL4 | C-C chemokine ligand 3; a.k.a. MIP-1β |
| IL8 | Interleukin-8 |
| LTF | Lactotransferrin |
| ELA2 | Neutrophil elastase 1 |
| IL1A | Interleukin 1α |

Statistical Analysis

Initially, data were described using medians, interquartile ranges (IQR), frequencies, and percents. Comparisons between survivors and non-survivors were performed using the Mann-Whitney U-test, Chi-square test, or Fisher's Exact test as appropriate. Analysis of descriptive statistics and comparisons were performed using SigmaStat Software (Systat Software, Inc., San Jose, Calif., USA).

Serum levels of the 12 biomarkers were used to generate a classification and regression tree (CART) analysis, with a goal of predicting 28-day survival vs. death (Muller, R. and Mockel, M. Clin. Chim. Acta 394:1-6 (2008)). CART analysis is based on a binary recursive partitioning algorithm and allows for the discovery of complex predictor variable interactions that may not be apparent with more traditional methods, such as multiple linear regression. "Binary recursive partitioning" is so described, as the analysis is: 1) binary, meaning there were two possible outcome variables, namely "survival" and "death," with the effect of splitting patients into 2 groups; 2) recursive, meaning the analysis can be performed multiple times; and 3) partitioned, meaning the entire data set can be split into sections. This analysis also has the ability to eliminate predictor variables with poor performance. The Compumine Rule Discovery System (Compumine, found at http <colon slash slash> www <dot> compumine <dot> com <slash> web <slash> public <slash> home) was used for tree generation using the derivation cohort described above, consisting of 220 patients (23 non-survivors).

The decision tree was built using a leave-5-out cross-validation procedure, equal weight classification, and non-random variable selection. Specific criteria for pruning of the terminal classification daughter nodes were: 1) non-redundant appearance of a given biomarker within a branch, and 2) minimum number of subjects in at least one daughter node ≥5% relative to the root node.

To derive the decision tree, the CART approach was used to determine biomarker cutoffs (Muller, R. et al. Clinica Chimica Acta, 394:1-6 (2008)). All 12 candidate biomarkers, as well as age and gender were considered in the CART analysis. The classification tree was built using Salford Predictive Modeler v6.6 (Salford Systems, San Diego, Calif., USA). Performance of the decision tree is reported using diagnostic test statistics with 95% confidence intervals computed using the score method as implemented by VassarStats Website for Statistical Computation (found at http <colon slash slash> faculty <dot> vassar <dot> edu <slash> lowry <slash> VassarStats <dot> html).

Results

The demographics and clinical characteristics of the derivation cohort (n=220) are provided in Table 4. The 23 (10.5%) non-survivors had a higher median PRISM score compared to the 197 survivors. Age, gender, race, infection characteristics, and occurrence of co-morbidities did not differ significantly between survivors and non-survivors. The mean±SD and median (IQR) times to death in the derivation cohort nonsurvivors were 6.1±7.5 and 2 (1 to 8) days, respectively. A complete list of co-morbidities for the survivors in the derivation cohort is provided in Table 5. A list of causative organisms for the derivation cohort is provided in Table 6.

TABLE 4

Demographics and clinical characteristics of the derivation cohort.

|  | All | Survivors | Non-survivors |
|---|---|---|---|
| Number of subjects | 220 | 197 | 23 |
| Median age in years (25%, 75%)[1] | 2.2 (0.8, 5.9) | 2.3 (1.0, 5.9) | 1.4 (0.2, 4.2) |
| Median PRISM score (25%, 75%) | 15 (8, 22) | 13 (7, 20) | 28 (20, 37)[2] |
| Number of males (%) | 137 (62) | 120 (61) | 17 (74) |
| Number of females (%) | 83 (38) | 77 (39) | 6 (26) |
| Number for race (%) | 153 (70) | 138 (70) | 15 (65) |
| Caucasian | 39 (18) | 35 (17) | 4 (17) |
| African American | 12 (5) | 11 (6) | 1 (4) |
| Other[3] | 16 (7) | 13 (7) | 3 (13) |
| Ureported |  |  |  |
| Number with gram (+) bacteria (%) | 70 (32) | 61 (31) | 9 (39) |

TABLE 4-continued

Demographics and clinical characteristics of the derivation cohort.

|  | All | Survivors | Non-survivors |
|---|---|---|---|
| Number with gram (−) bacteria (%) | 55 (25) | 51 (26) | 4 (17) |
| Number with viral infection (%) | 16 (7) | 13 (7) | 3 (13) |
| Number with fungal infection (%) | 7 (3) | 6 (3) | 1 (4) |
| Number with no organism isolated (%) | 72 (33) | 66 (34) | 6 (26) |
| Number with any co-morbidity (%) | 91 (41) | 82 (42) | 9 (39)[4] |
| Number with meningitis (%) | 12 (5) | 10 (5) | 2 (9) |
| Number with cancer (%) | 17 (5) | 17 (9) | 0 (0) |
| Number with immune suppression (%)[5] | 16 (7) | 13 (7) | 3 (13) |

[1] Two subjects in the derivation cohort were older than stated in the protocol (13 and 14 years of age) but were included in the analysis.
[2] $P < 0.001$ vs. survivors.
[3] Includes Asian, multi-racial, native Hawaiian/Pacific Islander, and American Indian.
[4] Co-morbidities in non-survivors included anti-phospholipid antibody syndrome, aplastic anemia, chronic lung disease (2 subjects), DiGeorge Syndrome, developmental delay (2 subjects), hypoplastic left heart syndrome, and short gut syndrome.
[5] Refers to patients with immune suppression not related to cancer (for example, those receiving immune suppressive medication for solid organ transplantation, or those with a primary immune deficiency).

TABLE 5

List of co-morbidities in survivors for the derivation and test cohorts.

| Derivation Cohort (N) | Test Cohort (N) |
|---|---|
| Developmental Delay (15) | Bone marrow transplantation (9) |
| Bone marrow transplantation (7) | Acute lymphocytic leukemia (6) |
| Unspecified congenital heart disease (6) | Developmental delay (4) |
| Acute lymphocytic leukemia (4) | Medulloblastoma (3) |
| Short gut syndrome (4) | Unspecified congenital heart disease (3) |
| Drowning (3) | Acute myeloid leukemia (2) |
| Liver transplant (3) | Down Syndrome (2) |
| Neuroblastoma (3) | Aplastic anemia (1) |
| Severe combined immune deficiency (3) | Chronic granulomatous disease (1) |
| Unspecified brain tumor (3) | Chronic lung disease (1) |
| Glycogen storage disease type 1 (2) | DiGeorge Syndrome (1) |
| Hemophagocytic lymphohistiocytosis (2) | End stage renal disease (1) |
| Down Syndrome (2) | Hepatoblastoma (1) |
| Mitochondrial disorder (2) | Hypoplastic left heart syndrome (1) |
| Subglottic stenosis (2) | IPEX Syndrome (1) |
| Aplastic anemia (1) | Liver and Bowel Transplant (1) |
| Atrial and ventricular septal defects (1) | Multi-visceral transplant (1) |
| Caustic ingestion (1) | Multiple congenital anomalies (1) |
| Chronic lymphopenia (1) | Nephrotic syndrome (1) |
| Cyclic Neutropenia (1) | Obstructed pulmonary veins (1) |
| Cri Du Chat syndrome (1) | Prader-Willi Syndrome (1) |
| End stage renal disease (1) | Sarcoma (1) |
| Heterotaxy (1) | Sickle cell disease (1) |
| Hydrocephalus (1) | Small bowel transplant (1) |
| Kidney transplant (1) | Trisomy 18 (1) |
| Langerhans cell histiocytosis (1) | Wilms tumor (1) |
| Liver failure (1) | |
| Medulloblastoma (1) | |
| Metaleukodystrophy (1) | |
| Neuromuscular disorder (1) | |
| Pallister Killian Syndrome (1) | |
| Prader-Willi Syndrome (1) | |
| Retinoblastoma (1) | |
| Rhabdomyosarcoma (1) | |
| Rhabdosarcoma (1) | |
| Seizure disorder (1) | |
| Sleep apnea (1) | |
| Tracheal stenosis (1) | |
| Traumatic brain injury (1) | |
| Type 1 diabetes mellitus | |
| Unspecified leukemia (1) | |
| VATER Syndrome (1) | |

TABLE 6

Causative organisms for derivation and test cohorts.

| Organism | Derivation Cohort (#) | Test Cohort (#) |
|---|---|---|
| *Acinetobacter baumannii* | 1 | 0 |
| Adenovirus | 1 | 0 |
| *Bacteroides* species | 1 | 0 |
| *Candida* species | 4 | 0 |
| *Capnocytophaga jenuni* | 0 | 1 |
| Cytomegalovirus | 1 | 0 |
| *Enterobacter cloacae* | 3 | 4 |
| *Enterococcus faecalis* | 4 | 1 |
| *Escherichia coli* | 2 | 1 |
| Herpes simplex virus | 2 | 2 |
| Human metapneumovirus | 0 | 1 |
| Influenza A | 4 | 4 |
| *Klebsiella pneumoniae* | 9 | 2 |
| *Micrococcus* species | 0 | 1 |
| Mixed | 23 | 14 |
| *Moraxella catarrhalis* | 1 | 0 |
| *Neisseria meningitidis* | 9 | 4 |
| Parainfluenza | 1 | 0 |
| *Pseudomonas* species | 3 | 2 |
| *Serratia marcescens* | 0 | 1' |
| *Staphylococcus aureus* | 11 | 6 |
| *Streptococcus agalactiae* | 3 | 3 |
| *Streptococcus milleri* | 1 | 0 |
| *Streptococcus pneumoniae* | 7 | 5 |
| *Streptococcus pyogenes* | 17 | 2 |
| Unspecified gram negative rod | 5 | 5 |
| Unspecified gram positive cocci | 6 | 3 |

The derived decision tree following CART analysis of the derivation cohort is depicted in FIG. 2. Maximum accuracy was achieved with 5 of the 12 candidate stratification biomarker gene probes, namely CCL3, LCN2, HSPA1B, IL8, and ELA2 (Table 7). No demographic or clinical variables were found to improve predictive accuracy in this decision tree.

TABLE 7

List of 5 biomarker gene probes selected for decision tree from derivation cohort.

| Gene Symbol | Description |
|---|---|
| CCL3 | C-C chemokine ligand 3; a.k.a. MIP-1α |
| LCN2 | Lipocalin 2; a.k.a. NGAL |
| HSPA1B | Heat shock protein 70 kDa 1B |
| IL8 | Interleukin-8 |
| ELA2 | Neutrophil elastase 1 |

Calculations of model performance were conducted using a 2×2 contingency table for the application of the decision tree to the derivation cohort was then developed, showing true positives, true negatives, false positives, and false negatives. This table allows for the calculation of performance characteristics, such as sensitivity, specificity, positive predictive value (PPV), negative predictive value (NPV), likelihood ratio (LR), and confidence interval (CI), as shown in FIG. 3. All patients in low risk terminal nodes were predicted as survivors in the contingency table, whereas all patients in high risk nodes were predicted as non-survivors in the contingency table.

As shown in FIG. 2, the tree contained 5 decision rules and 10 daughter nodes. The tree contained three low risk terminal nodes (≤1.5% risk of death; nodes 5, 8, and 9) and three high-risk terminal nodes (≥40% risk of death, nodes 2, 4, and 10). Of the 171 participants classified as low-risk, 169 survived, and 2 (1.2%) had died by 28 days. Of the 49 participants classified as high risk, 21 (42.9%) had died by 28 days.

Example 3

Validation of Persevere

In a subsequent study, the PERSEVERE classification tree generated using the derivation cohort described in Example 2 was prospectively applied to a separate, independent test cohort of children with septic shock.

Patients

This study was conducted on an independent test cohort of 135 pediatric patients with septic shock, of whom 18 (13.3%) did not survive to 28 days. This mortality rate is consistent with reported epidemiology for the United States (Watson, R. et al. *Am. J. Respir. Crit. Care Med.* 167:695-701 (2003)). All patients had serum samples taken during the first 24 hours of presentation to the pediatric intensive care unit. All serum samples were extensively annotated with clinical data.

After informed consent, one blood sample (5 ml) was obtained within 24 hrs of admission to the PICU of children (<10 years of age) with septic shock, or within 24 hours of meeting criteria for septic shock in patients already in the PICU. Septic shock was defined based on published, pediatric-specific criteria, which were identical to that used for enrollment of the existing derivation cohort (Goldstein, B. et al. *Pediatr. Crit. Care Med.* 6:2-8 (2005)). The restriction to patients ≤10 years of age reflects the specific intent to study a population strictly composed of "children," as has been done previously with the genomic data base and derivation cohort. Patients within this age group will universally be pre-pubertal, thereby excluding the adolescent age range that more approximates the adult population.

Samples were immediately processed and stored at −20° C. Clinical data were recorded at study entry and daily (up to 28 days) using the database described above. The extensive clinical variables that were recorded include physiological and laboratory parameters representing multiple organ systems, blood component transfusions, and demographics. Biological samples were matched to clinical data using the BSTS. The presence or absence of organ failure was recorded daily, based on published, pediatric-specific criteria (Goldstein, B. et al. *Pediatr. Crit. Care Med.* 6:2-8 (2005)). The only exclusion criteria were the inability to obtain informed consent, or if the attending physician caring for the patient deemed that removing an additional 5 ml of blood would be deleterious to the patient.

Standard clinical care was not under protocol for the enrolled subjects. Patients were followed for 28 days to determine survival. Accordingly, all mortality-related data refer to this 28 day period.

CART Analysis

To validate the risk model, the classification tree derived in Example 2 was applied to the prospectively collected data. The same candidate biomarker gene probes were measured, and patients in the test cohort were "dropped" through the classification tree. Outcome predictions and performance calculations were conducted in an identical manner as described in Example 2 above. As shown in FIG. 4, the tree for the test cohort contained the same 3 low risk terminal nodes and 3 high risk terminal nodes. The 2×2 contingency table for the test cohort is shown in FIG. 5.

Results

Table 8 provides the demographic and clinical characteristics of the test cohort. Compared to the derivation cohort, the test cohort had a higher proportion of Caucasians and a greater proportion with no causative organism isolated. The test cohort also had a lower proportion with no reported race and a lower proportion with gram-positive bacteria, compared to the derivation cohort. The test and derivation cohorts were otherwise not statistically different. Within the test cohort, there were no significant differences between survivors and non-survivors, except for the median PRISM scores. The mean and median times to death in the test cohort non-survivors were 9.9±SD 11.2 and 4 (IQR 2 to 16) days, respectively. A complete list of co-morbidities for the survivors in the test cohort is provided in Table 5. A list of causative organisms for the test cohort is provided in Table 6.

The classification of the test cohort participants according to the decision tree is shown in FIG. 4. Seventy-seven patients were classified as low risk (nodes 5 and 8), while 58 were classified as high risk (nodes 2, 4, and 10). Among the low-risk participants, the mortality rate was 2.6%, while among the high-risk participants the mortality rate was 27.6%.

TABLE 8

Demographics and clinical characteristics of the test cohort.

|  | All | Survivors | Non-survivors |
| --- | --- | --- | --- |
| Number of subjects | 135 | 117 | 18 |
| Median age in years (25%, 75%) | 2.8 (1.0, 6.7) | 2.7 (1.0, 6.7) | 3.8 (0.9, 7.7) |
| Median PRISM score (25%, 75%) | 13 (7, 19) | 12 (7, 18) | 23 (14, 32)[1] |
| Number of males (%) | 70 (52) | 63 (54) | 7 (39) |
| Number of females (%) | 65 (48) | 54 (46) | 11 (61) |
| Number for race (%) |  |  |  |
| Caucasian | 113 (84)[2] | 99 (85) | 14 (78) |
| African American | 15 (11) | 13 (11) | 2 (11) |
| Other[3] | 6 (4) | 4 (3) | 2 (11) |
| Unreported | 1 (1)[2] | 1 (1) | 0 (0) |
| Number with gram (+) bacteria (%) | 27 (20)[2] | 24 (21) | 3 (17) |
| Number with gram (−) bacteria (%) | 27 (20) | 22 (19) | 5 (28) |

TABLE 8-continued

Demographics and clinical characteristics of the test cohort.

|  | All | Survivors | Non-survivors |
|---|---|---|---|
| Number with viral infection (%) | 10 (7) | 9 (8) | 1 (6) |
| Number with fungal infection (%) | 2 (1) | 2 (2) | 0 (0) |
| Number with no organism isolated (%) | 72 (53)[2] | 63 (54) | 9 (50) |
| Number with any co-morbidity (%) | 52 (39) | 45 (38) | 7 (39)[4] |
| Number with meningitis (%) | 5 (4) | 3 (3) | 2 (11) |
| Number with cancer (%) | 17 (13) | 14 (12) | 3 (17) |
| Number with immune suppression (%)[5] | 13 (10) | 13 (11) | 0 (0) |

[1]P = 0.001 vs. survivors.
[2]P < 0.05 for test cohort vs. derivation cohort.
[3]Includes Asian, multi-racial, native Hawaiian/Pacific Islander, and American Indian.
[4]Co-morbidities in non-survivors included acute myeloid leukemia, atrial and ventricular septal defects, fulminant hepatic failure, hypoplastic left heart syndrome, short gut syndrome, neuroblastoma, and optic nerve glioma.
[5]Refers to patients with immune suppression not related to cancer (for example, those receiving immune suppressive medication for solid organ transplantation, or those with a primary immune deficiency).

Example 4

Combined Results from Derivation and Test Cohorts

In a subsequent study, the results from the derivation and test cohort studies, described in Examples 2 and 3 above, were combined. As shown in FIG. 6, the tree contained the same 3 low risk terminal nodes and 3 high risk terminal nodes. The 2×2 contingency table for the derivation and test cohorts is shown in FIG. 7. These results can be used to predict the likelihood of a particular outcome.

Example 5

Use of Secondary Considerations to Develop Updated Decision Tree

The classification tree was updated using all 355 participants in the combined derivation and test cohorts. All 12 candidate biomarkers, as well as age and gender were considered in the updating process.

The updated decision tree is shown in FIG. 8. Maximum accuracy was achieved with three of the same stratification biomarkers (CCL3, HSPA1B, and IL8), while the importance of ELA2 and LCN2 were superseded by GZMB and MMP8. Age also added to the predictive capacity of the updated tree (nodes 13 and 14).

There were three low-risk terminal nodes (0.0 to 2.5% mortality probability; nodes 7, 11, and 14) and five high-risk terminal nodes (18.2 to 62.5% mortality probability; nodes 4, 8, 10, 12, and 13). Of the 236 participants classified as low risk, 233 survived (98.7%) and 3 had died (1.3%) by 28 days. Of the 119 participants classified as high risk, 38 had died (31.9%) by 28 days. The diagnostic test characteristics of the updated decision tree are shown in Table 9, along with the results from the derivation and test cohorts with the original classification tree.

TABLE 9

Performance of the classification trees.

|  | Derivation cohort | Test cohort | Updated model |
|---|---|---|---|
| Number of subjects | 220 | 135 | 355 |
| Number of true positives | 21 | 16 | 38 |
| Number of true negatives | 169 | 75 | 233 |
| Number of false positives | 28 | 42 | 81 |
| Number of false negatives | 2 | 2 | 3 |
| Sensitivity | 91% (70, 98) | 89% (64, 98) | 93% (79, 98) |
| Specificity | 86% (80, 90) | 64% (55, 73) | 74% (69, 79) |
| Positive predictive value | 43% (29, 58) | 28% (17, 41) | 32% (24, 41) |
| Negative predictive value | 99% (95, 100) | 97% (90, 100) | 99% (96, 100) |
| +Likelihood ratio | 6.4 (4.5, 9.3) | 2.5 (1.8, 3.3) | 3.6 (2.9, 4.4) |
| −Likelihood ratio | 0.1 (0.0, 0.4) | 0.2 (0.0, 0.6) | 0.1 (0.0, 0.3) |
| Area under the curve | 0.885 | 0.759 | 0.883 |

From these PERSEVERE results, the 81 false-positive participants in the updated decision tree (that is, those predicted to be non-survivors, but were actually survivors) are likely to demonstrate an increased degree of organ dysfunction and PICU LOS, and fewer PICU-free days, compared to the 233 true-negative participants (that is, those predicted to be survivors and were actually survivors). Thirty percent of the false-positive participants had persistence of two or more organ failures at 7 days after study entry, compared to only 9% of the true-negative participants (P<0.001). The median (IQR) PICU LOS for the false positive participants was 11 (6 to 17) days, compared to 7 (4 to 12) days for the true-negative participants (P=0.003). Additionally, 64% of the false-positive participants had a PICU LOS >1 week, compared to 46% of the true-negative participants (P=0.01). The median number of PICU-free days for the false-positive participants was 18 (12 to 23) days, compared to 21 (16 to 25) days for the true-negative participants (P=0.006). Additionally, 58% of the false-positive participants had <21 PICU-free days, compared to 44% of the true negative participants (P=0.025).

As shown in Table 10, the updated PERSEVERE model has a higher area under the curve than PRISM. In addition, at a comparable sensitivity of 93%, the PPV and specificity of PERSEVERE are 2-fold higher than that of PRISM.

TABLE 10

Comparison of PERSEVERE and PRISM for predicting mortality in the combined derivation and test cohorts.

|  | Calibrated PERSEVERE | PRISM at Sensitivity = PERSEVERE | PRISM at Specificity = PERSEVERE |
|---|---|---|---|
| Number of Subjects | 355 | 353[1] | 353[1] |
| True Positives | 38 | 37 | 29 |
| True Negatives | 233 | 120 | 234 |
| False Positives | 81 | 193 | 79 |
| False Negatives | 3 | 3 | 11 |
| Sensitivity | 93% (79-98) | 93% (79-98) | 73% (56-85) |
| Specificity | 74% (69-79) | 38% (33-44) | 75% (69-79) |
| Positive Predictive Value | 32% (24-41) | 16% (12-22) | 27% (19-36) |
| Negative Predictive Value | 99% (96-100) | 98% (92-99) | 96% (92-98) |
| +Likelihood Ratio | 3.6 (2.9-4.4) | 1.5 (1.3-1.7) | 2.3 (2.2-3.8) |
| −Likelihood Ratio | 0.1 (0.0-0.3) | 0.2 (0.1-0.6) | 0.4 (0.2-0.6) |
| Area under the curve | 0.883 | 0.798 | 0.798 |

[1]Two participants (1 survivor and 1 non-survivor) did not have PRISM scores recorded.

Example 6

Optimization of Persevere

The method of developing the PERSEVERE model, as described in Examples 2-3 and 5 above, is reiterated in a larger pediatric patient cohort to develop a decision tree with additional branches and/or nodes in order to further improve model performance. Biomarker gene probes that were not selected in Examples 2 and 5 are included in an optimized model, which can include additional biomarker gene probes from Tables 1, 2, or 3.

Example 7

Stratification of Pediatric Septic Shock Patients for Clinical Trials

PERSEVERE is used to stratify pediatric septic shock patients for high risk clinical trials. A patient is subjected to the PERSEVERE decision tree described herein. The patient is then classified into an outcome risk category, based on the model: low risk (≤18% mortality probability), moderate risk (18 to 40% mortality probability), and high risk (≥40% mortality probability). A patient categorized as moderate or high risk is then selected for one or more high risk interventions.

Alternatively, PERSEVERE is used to stratify pediatric septic shock patients for low risk clinical trials. A patient is subjected to the PERSEVERE decision tree described herein. The patient is then classified into an outcome risk category, based on the model: low risk (≤18% mortality probability), moderate risk (18 to 40% mortality probability), and high risk (≥40% mortality probability). A patient categorized as low risk is then selected for one or more low risk interventions.

Example 8

Individualized Treatment Decisions for Septic Shock Patients

PERSEVERE is used to make individual patient decisions at the bedside (point of care) for the pediatric patient. PERSEVERE is used to make clinical decisions given the rapid turnaround time of the analysis. The PERSEVERE panel also is used to select the pediatric patients most likely to benefit from a particular treatment or exclude pediatric patients who are predicted to do well with standard care. The panel is used to select the pediatric patients most likely to benefit from a particular treatment; the panel also is used to exclude pediatric patients who are predicted to do well with standard care.

Example 9

Quality Improvement for Treatment of Pediatric Septic Shock Patients

PERSEVERE is used as a tool for quality improvement. The model serves as a metric for institutions to measure their respective outcomes in pediatric patients with septic shock. If a substantial number of pediatric septic shock patients are not surviving, PERSEVERE is used to evaluate their patient risk profiles and subsequently to examine their clinical processes. Alternatively, if an institution has a large number of high risk pediatric patients who are surviving in disproportionately high ratios, then PERSEVERE is used to study those patients and evaluate their treatment based on their risk profiles.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of classifying a pediatric patient with septic shock as high risk or low risk, the method comprising:
    identifying a pediatric patient with septic shock;
    obtaining a sample from the patient;
    analyzing the sample to determine the level(s) of one or more biomarkers selected from the group consisting of the biomarkers listed in Table 1, wherein the one or more biomarkers comprise all of C-C chemokine ligand 3 (CCL3), heat shock protein 70 kDa 1B (HSPA1B), interleukin-8 (IL8), lipocalin 2 (LCN2), and elastase 2 (ELA2);
    determining whether the level(s) of the one or more biomarkers are elevated above a cut-off level, wherein the presence of an elevated level of one or more biomarkers associated with septic shock in pediatric patients indicates that the patient has an elevated likelihood of being classified as high risk and the absence of an elevated level of one or more biomarkers associated with septic shock in pediatric patients indicates that the patient has a reduced likelihood of being classified as high risk,
    wherein a classification of high risk comprises:
        a) an elevated level of CCL3, or
        b) a non-elevated level of CCL3 and an elevated level of HSPA1B, or
        c) non-elevated levels of CCL3, HSPA1B, and ELA2, and elevated levels of IL8 and LCN2;
    and wherein a classification of low risk comprises:
        d) non-elevated levels of CCL3, HSPA1B, and IL8, or
        e) non-elevated levels of CCL3 and HSPA1B, and elevated levels of IL8 and ELA1, or
        f) non-elevated levels of CCL3, HSPA1B, ELA2, and LCN2, and an elevated level of IL8.

2. The method of claim 1, wherein
    a) an elevated level of CCL3 corresponds to a serum CCL3 concentration greater than 358 pg/ml,
    b) an elevated level of HSPA1B corresponds to a serum HSPA1B concentration greater than 3.3 μg/ml,
    c) an elevated level of IL8 corresponds to a serum IL8 concentration greater than 356 pg/ml,
    d) an elevated level of ELA2 corresponds to a serum ELA2 concentration greater than 345 ng/ml, and
    e) an elevated level of LCN2 corresponds to a serum LCN2 concentration greater than 8.7 ng/ml.

3. A method of classifying a pediatric patient with septic shock as high risk or low risk, the method comprising:
    identifying a pediatric patient with septic shock;
    obtaining a sample from the patient; analyzing the sample to determine the level(s) of one or more biomarkers selected from the group consisting of the biomarkers listed in Table 1, wherein the one or more biomarkers comprise all of C-C chemokine ligand 3 (CCL3), heat shock protein 70 kDa 1B (HSPA1B), interleukin-8 (IL8), granzyme B (GZMB), and matrix metalloproteinase-8 (MMP8),
    determining whether the level(s) of the one or more biomarkers are elevated above a cut-off level, wherein the presence of an elevated level of one or more biomarkers associated with septic shock in pediatric patients indicates that the patient has an elevated likelihood of being classified as high risk and the absence of an elevated level of one or more biomarkers associated with septic shock in pediatric patients indicates that the patient has a reduced likelihood of being classified as high risk,
    wherein a classification of high risk comprises
        a) elevated levels of CCL3, IL8, and GZMB, or
        b) a non-elevated level of IL8 and elevated levels of CCL3 and MMP8, or
        c) a non-elevated level of GZMB, elevated levels of CCL3 and IL8, and a patient age of 0.5 years or younger, or
        d) a non-elevated level of CCL3 and an elevated level of HSPA1B, or e) non-elevated levels of CCL3 and HSPA1B, and a highly elevated level of IL8, and wherein a classification of low risk comprises:
f) non-elevated levels of CCL3 and HSPA1B, and a non-highly elevated level of IL8 or
g) non-elevated levels of IL8 and MMP8 and an elevated level of CCL3, or
h) a non-elevated level of GZMB, elevated levels of CCL3 and IL8, and a patient age of older than 0.5 years.

4. The method of claim 3, wherein
a) an elevated level of CCL3 corresponds to a serum CCL3 concentration greater than 160 pg/ml,
b) an elevated level of HSPA1B corresponds to a serum HSPA1B concentration greater than 3.3 µg/ml,
c) an elevated level of IL8 corresponds to a serum IL8 concentration greater than 507 pg/ml,
d) a highly elevated level of IL8 corresponds to a serum IL8 concentration greater than 829 pg/ml,
e) an elevated level of GZMB corresponds to a serum GZMB concentration greater than 55 pg/ml, and
f) an elevated level of MMP8 corresponds to a serum LCN2 concentration greater than 47.5 ng/ml.

5. The method of claim 1, wherein the determination of whether the level(s) of the one or more biomarkers are elevated is combined with one or more additional population-based risk scores.

6. The method of claim 5, wherein the one or more population-based risk scores comprises Acute Physiology and Chronic Health Evaluation II (APACHE) Pediatric Risk of Mortality (PRISM), Pediatric Index of Mortality (PIM), and/or PEdiatric Logistic Organ Dysfunction (PELOD).

7. The method of claim 1, wherein the sample is obtained within the first hour of presentation with septic shock.

8. The method of claim 1, wherein the sample is obtained within the first 48 hours of presentation with septic shock.

* * * * *